US007524653B2

(12) United States Patent
Nichols et al.

(10) Patent No.: US 7,524,653 B2
(45) Date of Patent: Apr. 28, 2009

(54) SMALL INTERFERING RNA LIBRARIES AND METHODS OF SYNTHESIS AND USE

(75) Inventors: Mark Nichols, Pittsburgh, PA (US); Richard Steinman, Pittsburgh, PA (US)

(73) Assignee: University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 725 days.

(21) Appl. No.: 10/842,353

(22) Filed: May 10, 2004

(65) Prior Publication Data

US 2007/0166720 A1 Jul. 19, 2007

Related U.S. Application Data

(60) Provisional application No. 60/469,169, filed on May 9, 2003.

(51) Int. Cl.
*C12N 15/64* (2006.01)
*C12N 15/00* (2006.01)
*C07H 21/04* (2006.01)

(52) U.S. Cl. ............... 435/91.41; 536/24.5; 435/91.42; 435/320.1

(58) Field of Classification Search ............... None
See application file for complete search history.

(56) References Cited

U.S. PATENT DOCUMENTS

| 5,646,037 | A | 7/1997 | Buxton |
| 6,506,559 | B1 | 1/2003 | Fire et al. |
| 6,573,099 | B2 | 6/2003 | Graham |
| 6,671,624 | B1 | 12/2003 | Dunlay et al. |
| 2003/0198627 | A1 | 10/2003 | Arts et al. |
| 2004/0115815 | A1 | 6/2004 | Li et al. |
| 2004/0146858 | A1 | 7/2004 | Li et al. |
| 2004/0224328 | A1 | 11/2004 | Prydz et al. |
| 2004/0224405 | A1 | 11/2004 | Leake et al. |
| 2005/0130184 | A1 | 6/2005 | Xu et al. |
| 2005/0142578 | A1 | 6/2005 | Usman et al. |

FOREIGN PATENT DOCUMENTS

| EP | 0 501 914 A | 9/1992 |
| WO | WO 02/44321 A3 | 6/2002 |
| WO | WO 03/020931 A2 | 3/2003 |
| WO | WO 03/027298 A1 | 4/2003 |

OTHER PUBLICATIONS

Kano et al., *Biomed. Biophys. Res. Comm.*, 248, 806-811 (1998).
Kawasaki et al., *Nucl. Acids Res.*, 31 (3), 981-987 (Feb. 1, 2003).
Sektas et al., *Mol. Biotechnol.*, 9 (1), 17-24 (Feb. 1998).
Trinh et al., *J. Immunol. Meth.*, 244 (1-2), 185-193 (Oct. 20, 2000).
Yoon et al., *Gene*, 223 (1-2), 67-76 (Nov. 26, 1998).
Chen et al., *Proceedings of the National Academy of Sciences of the United States of America*, 102(7), 2356-2361 (2005).
Abraham et al., *Trends in Biotechnology*, 22(1), 15-22 (2004).
Abraham et al., *Preclinica*, 2(5), 349-355 (2004).
Elsasser, *Proceedings of the National Academy of Sciences of the United States of America*, 81(16), 5126-5129 (1984).
Giuliano et al., *Journal of Biomolecular Screening*, 2(4), 249-259 (1997).
Giuliano, *Journal of Biomolecular Screening*, 8(2), 125-135 (2003).
Giuliano et al., *Assay and Drug Development Technologies*, 1(4) 565-577 (2003).
Li et al., *Proceedings of the National Academy of Sciences of the United States of America*, 101(5), 1350-1355 (2004).
Rubin, *Proceedings of the National Academy of Sciences of the United States of America*, 81(16), 5121-5125 (1984).
Hannon, *Nature*, 418(6894), 244-251 (2002).
Bhattacharya et al., *Proceedings of the National Academy of Sciences of the United States of America*, 99(13), 8838-8843 (2002).
Caplen et al., *Proceedings of the National Academy of Sciences of the United States of America*, 98(17), 9742-9747 (2001).
Danielian et al., *Molecular Endocrinology*, 7(2), 232-240 (1993).
Dobrovolsky et al., *Molecular Genetics and Metabolism*, 78(1), 1-10 (2003).
Elbashir et al., *Nature*, 411(6833), 494-498 (2001).
Fire et al., *Nature*, 391(6669), 806-811 (1998).
Gamper et al., *Biochemistry*, 42(9), 2643-2655 (2003).
Garcia et al., *Oncogene*, 21(55), 8379-8387 (2002).
He et al., *The Journal of Biological Chemistry*, 273(30), 18802-18811 (1998).
Kaykas et al., *BMC Cell Biology*, 5(16), 1-11 (2004).
MacDonald et al., *Journal of Molecular Biology*, 232(3), 1030-1047 (1993).

(Continued)

*Primary Examiner*—Richard Schnizer
(74) *Attorney, Agent, or Firm*—Leydig, Voit & Mayer, Ltd

(57) ABSTRACT

In one aspect, the invention provides a random or semirandom siRNA (encoding) library. Another aspect of the invention pertains to methods for construction of random or semirandom siRNA (encoding) libraries. Another aspect of the invention is vector systems for use in constructing siRNA libraries and/or that can express single siRNAs and siRNA libraries both constitutively and in an inducible fashion. In another aspect, the invention provides a method of using an siRNA library. The siRNA library is introduced into a population of cells. The population of cells then is subjected to a selection process to select a subpopulation of cells exhibiting a different behavioral, biochemical, chemical, functional, molecular, morphological, phenotypic, or physical property from the remainder of population. Following the selection process, the subpopulation of cells can be isolated, analyzed, and/or cloned as desired. Such analysis of the subpopulation can be identification and sequencing of the siRNA species responsible for the different properties of the subpopulation relative to the remainder of the population. Alternatively, the subpopulation can be further analyzed by genomic, proteomic, and/or cellomic assays. Where such genomic, proteomic, and/or cellomic assays are employed, the method can produce several useful bioinformatics products. Specific siRNAs identified through this process may have direct therapeutic value.

12 Claims, 16 Drawing Sheets

OTHER PUBLICATIONS

Muraoka et al., *Molecular and Cellular Biology*, 22(7), 2204-2219 (2002).
Mutsuddi et al., *Current Biology*, 14, 302-308 (2004).
Niwa et al., *Nature Genetics*, 24(4), 372-376 (2000).
Noirot et al., *The Journal of Biological Chemistry*, 273(20), 12274-12280 (1998).
Sadowski, *Progress in Nucleic Acid Research and Molecular Biology*, 51, 53-91 (1995).
Volpe et al., *Science*, 297(5588), 1833-1837 (2002).
Welsh et al., *Current Opinion in Biotechnology*, 8(5), 617-622 (1997).
Xiang et al., *Journal of Virology*, 76(10), 5251-5259 (2002).
Yu et al., *Molecular Therapy*, 7(1), 228-236 (2003).
U.S. Appl. No. 09/866,557, filed May 24, 2001, Beach et al.
U.S. Appl. No. 10/055,797, filed Jan. 22, 2002, Beach et al.
U.S. Appl. No. 10/255,568, filed Sep. 26, 2002, Tuschl et al.
U.S. Appl. No. 10/291,235, filed Nov. 8, 2003, Finney et al.
U.S. Appl. No. 10/301,516, filed Nov. 21, 2002, Shi et al.
U.S. Appl. No. 10/150,283, filed May 15, 2002, Ding et al.
U.S. Appl. No. 10/383,835, filed Mar. 6, 2003, Lorens.
U.S. Appl. No. 10/448,612, filed May 29, 2003, Yang et al.
U.S. Appl. No. 09/858,862, filed May 16, 2001, Beach et al.
U.S. Appl. No. 10/622,240, filed Jul. 18, 2003, Tzertzinis et al.
U.S. Appl. No. 10/441,923, filed May 19, 2003, Finney et al.
Aoki et al., "RNA interference may be more potent than antisense RNA in human cancer cell lines," Clin. Exp. Pharmacol. Physiol., 2003, 96-102, 30.
Aza-Blanc et al., "Identification of Modulators of TRAIL-Induced Apoptosis via RNAi-Based Phenotypic Screening," Molecular Cell, 2003, 627-637, 12.
Ashrafi et al., "Genome-wide RNAi analysis of *caenorhabditis elegans* fat regulatory genes," Nature, 2003, 268-72, 421.
Berns et al., "A large-scale RNAi screen in human cells identifies new components of the p53 pathway," Nature, 2004, 431-37, 428.
Bertrand et al., "Comparison of antisense oligonucleotides and siRNAs in cell culture and in vivo," Biochem. Biophys. Res. Commun., 2002, 1000-4, 296.
Boutros et al., "Genome-wide RNAi analysis of growth and viability in drosophila cells," Science, 2004, 832-5, 303.
Brummelkamp et al., "A system for Stable Expression of Short Interfering RNAs in Mammalian Cells," Science, 2002, 550-553, 296.
Couzin et al., Breakthrough of the year, "Small RNAs make big splash," Science 2002, 2296-7, 298.
Czauderna et al., "Inducible shRNA expression for application in a prostate cancer mouse model," Nucleic Acids Res., 2003, e127, 31.
Devroe et al., "Retrovirus-delivered siRNA," BMC Biotechnology, 2002, 1-5, 2(15).
Hall et al., "RNA interference machinery regulates chromosome dynamics during mitosis and meiosis in fission yeast," Proc. Natl. Acad. Sci. U S A, 2003, 193-8, 100.
Hingorani et al., "Suppression of BRAF(V599E) in human melanoma abrogates transformation," Cancer Res., 2003, 5198-202, 63.
Howard; "Unlocking the money-making potential of RNAi," Nat. Biotechnol., 2003, 1441-6, 21.

Kamath et al., "Effectiveness of specfic RNA-mediated interference through ingested double-stranded RNA in *caenorhabditis* elegans," Genome Biology, 2000, 0002.1-0002.10, 2.
Kamath et al., "Systematic functional analysis of the Caenorhabditis elegans genome using RNAi," Nature, 2003, 231-7, 421.
Kennedy, "Breakthrough of the year," Science, 2002, 2283, 298.
Kitabwalla et al., "RNA interference—a new weapon against HIV and beyond," N. Engl. J. Med., 2002, 1364-7, 347.
Luo et al., "Small interfering RNA production by enzymatic engineering of DNA (SPEED)," Proc. Natl. Acad. Sci. U S A, 2004, 5494-9, 101.
McCaffrey et al., "Inhibition of hepatitis B virus in mice by RNA interference," Nat. Biotechnol., 2003, 639-44, 21.
McCaffrey et al., "RNA interference in adult mice," Nature, 2002, 38-9, 418.
Miyagishi et al., "U6 promoter-driven siRNAs with four uridine3' overhangs efficiently suppress targeted gene expression in mammalian cells," Nature Biotechnology, 2002, 497-500, 19.
Miyagishi et al., "Generation of an shRNAi expression library against the whole human transcripts," Virus Research, 2004, 117-24, 102.
Paddison et al., "Short hairpin RNAs (shRNAs) induce sequence-specific silencing in mammalian cells," Genes & Development, 2002, 948-958, 16.
Paddison et al., "A resource for large-scale RNA-interference-based screens in mammals," Nature, 2004, 427-31, 428.
Paul et al., "Effective expression of small interfering RNA in human cells," Nature Biotechnology, 2002, 505-508, 29.
Reich et al., "Small interfering RNA (siRNA) targeting VEGF effectively inhibits ocular neovascularization in a mouse model," Mol. Vis., 2003, 210-6, 9.
Schramke et al., "Hairpin RNAs and retrotransposon LTRs effect RNAi and chromatinbased gene silencing," Science, 2003, 1069-74, 301.
Semizarov et al., "Specificity of short interfering RNA determined through gene expression signatures," Proc. Natl. Acad. Sci. U S A, 2003, 6347-52, 100.
Sen et al., "Restriction enzyme-generated siRNA (REGS) vectors and libraries," Nat, Genet, 2004, 183, 36.
Shirane et al., "Enzymatic production of RNAi libraries from cDNAs," Nat. Genet., 2004, 190, 36.
Sui et al., "A DNA vector-based RNAi technology to suppress gene expression in mammalian cells," PNAS, 2002, 5515-5520, 99(8).
Suyama et al., "Identification of genes involved in cell invasion by using a library of randomized hybrid ribozymes," Proc. Natl. Acad. Sci. U, S A, 2003, 561621, 100.
Tijsterman et al., "Dicers at RISC: The mechanism of RNAi," 2004, 1-4, 117.
Tuschl, "RNA sets the standard," Nature, 2003, 220-21, 421.
Wall et al., "Small RNA: can RNA interference be exploited for therapy?" Lancet, 2003; 1401-3, 362.
Zheng et al., "An approach to genomewide screens of expressed small interfering RNAs in mammalian cells," Proc. Natl. Acad. Sci U S A., 2004, 135-40, 101.

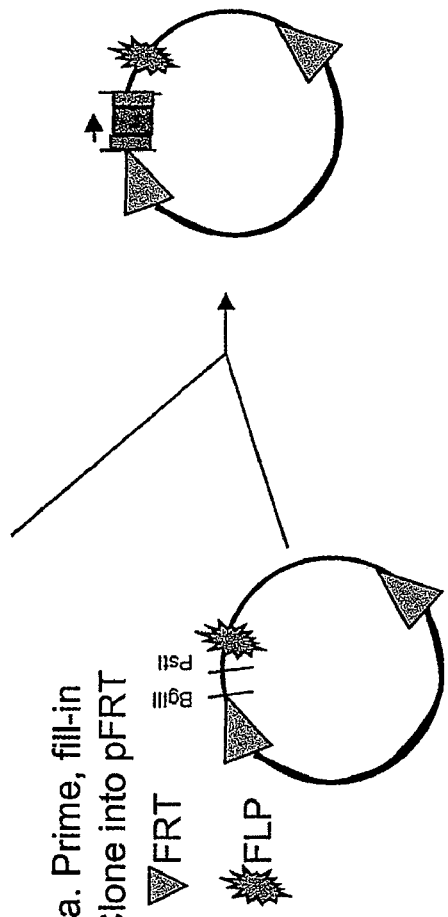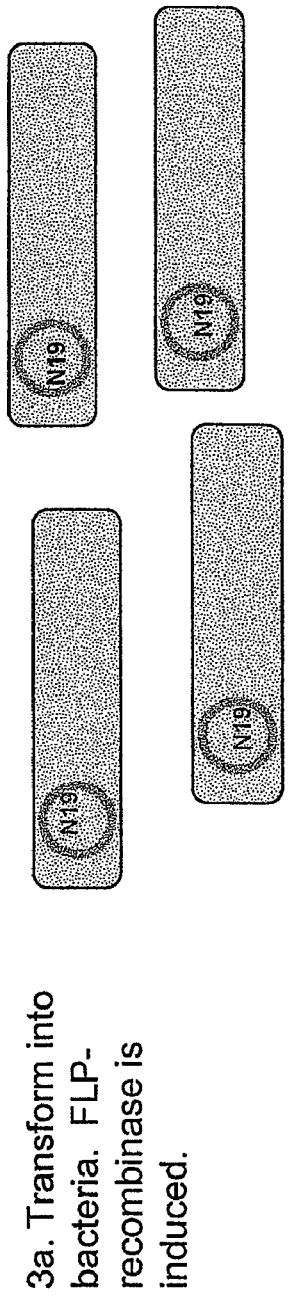
Figure 1A
METHOD 1A-hairpin
1a. Generate n(19) random sequences bounded by unique restriction sites (eg Asc1 or Fse1)
CCCAGATCTGNNNNNNNNNNNNNNNNNNNCTGCAGACG (SEQ ID NO: 51)
BglII                                                               PstI
2a. Prime, fill-in Clone into pFRT
▽ FRT
✻ FLP
3a. Transform into bacteria. FLP-recombinase is induced.

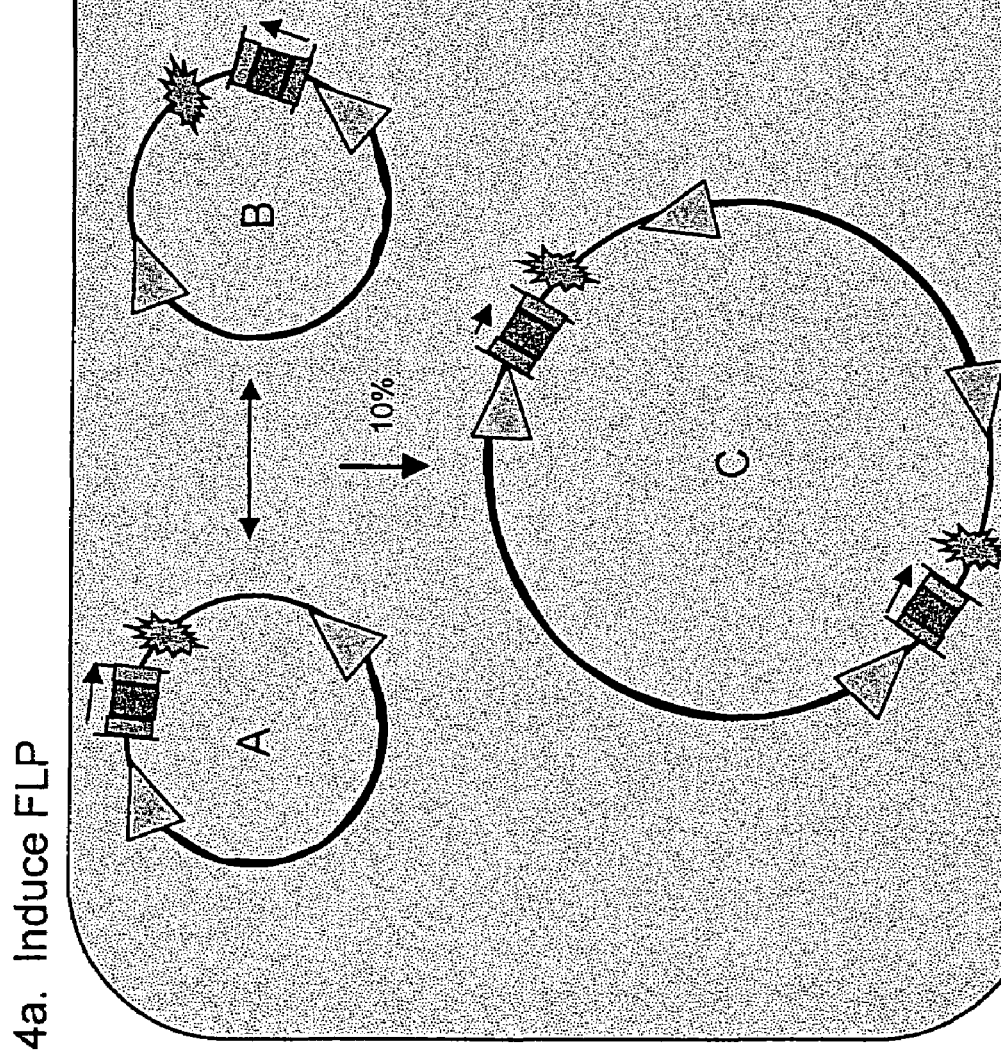

Method 1B-making an Inducible library (and inducible specific siRNAs) based on inducible FLP Proceed as in method 1A through step 5a with the following change:

7d. Digest with PstI and religate

U6 transcription of the siRNA is interrupted by a proximal termination sequence so no siRNA is transcribed Because both FRT are in same orientation, addition of FLP resolves them into 1 FRT and removes upstream sequence including terminator Example of inducible library plasmid (in pMIG) in which siRNA is made in the presence of tamoxifen (which liberates FLP).

Figure 3
Method 1C–making an Inducible library based on inducible T7-polymerase
Proceed as in method 1A through step 5a
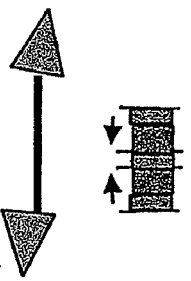
6c. Clone "C" library into T7 polymerase site
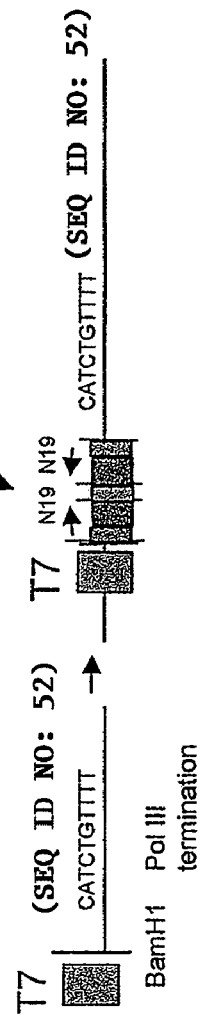
7c. Recipient vector has tamoxifen-inducible T7 polymerase (polymerase cloned as fusion gene with estrogen receptor inducible domain).
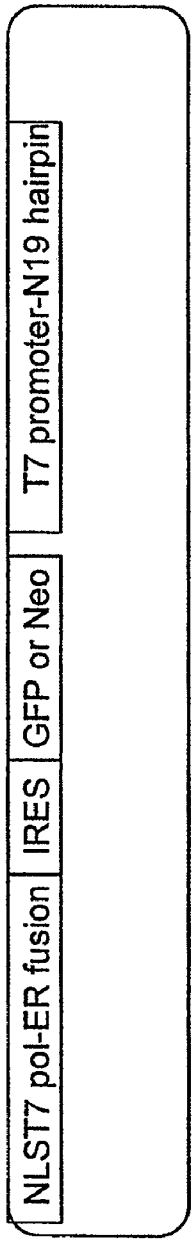

Figure 4B

METHOD 2b-bidirectional based upon polymerase III promoters

1. Generate n(19) random sequences followed by 3' by a termination site(TTTTT) and flanked by restriction sites(eg Sal1 and Cla1 for cloning into pMIG). 5'Sal1-NNNNNNNNNNNNNNNNNNNNTTTTT-Cla-1 (SEQ ID NO: 53)

2. Prime, fill-in
Clone into a vector with opposing U6 promoters (pMIG retroviral example below)

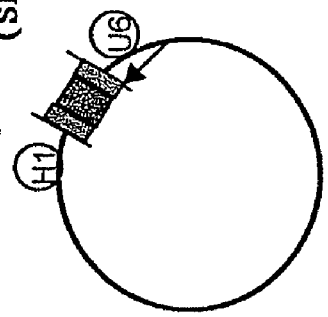

| Gene whose pathway is to be analyzed | IRES | GFP or Neo | U6 | N19 | U6 |

METHOD 3–bidirectional based upon T7 promoter

Figure 5

- Generate n(19) random sequences flanked distally by a class II T7 stop sequence in opposite orientations and proximally by a T7 promoter in opposite orientations.

```
       STOP                      T7                  N19                    T7               STOP
         ↓                        ↑                   ↕                      ↓                ↑
5' R1-AAAACAGATGAAGATAATACGACTCACTATAGGNNNNNNNNNNNNNNNNNNNCC TATAGTGAGTCGTATTATGCT CATCTGTTT-R2  (SEQ ID NO: 54)
     TTTT GTCTAC TTCT ATTATGCTGAGTGATATCC NNNNNNNNNNNNNNNNNNNGGATATCACTCAGCATAATACGAGTAGACAAA  5' (SEQ ID NO: 55)
```

R1 and R2 are convenient restriction sequences for cloning; orange nucleotides are spacers. This generates messages:

Sense: N19--T7rev-Stop and Antisense: N19- T7rev-Stop Only the N19 sequence anneals to form double stranded RNA.

Example of usable construct in pMIG vector:

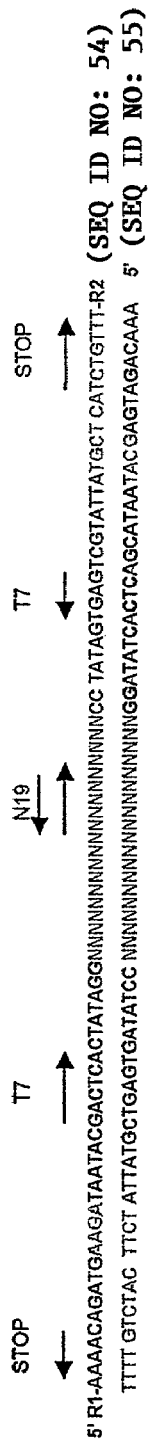

Or in a tamoxifen-inducible form:

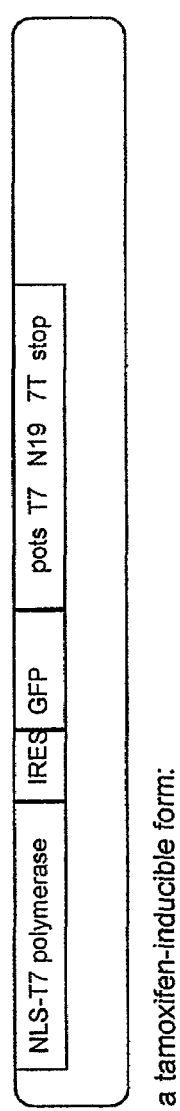

Figure 6A

METHOD 4

1. Generate n(19) random sequences bounded by a 5' restriction site (eg Xho1) and a 3' loop followed by a self-annealing sequence to prime reverse-strand synthesis.

```
                                      G
GTCGCTCGAGAANNNNNNNNNNNNNNNNNNNGGCCA      (SEQ ID NO: 56)
                               ||||||
                               CCGGG
                                    A
   Xho1
```

2. Prime reverse-strand synthesis.

```
                                                  G
GTCGCTCGAGAANNNNNNNNNNNNNNNNNNNGGCCA               (SEQ ID NO: 57)
CAGCGAGCTCTTNNNNNNNNNNNNNNNNNNNNNN CCGGG
                                        A
```

Figure 6B

2. Denature double strand and elute 74-bp sequences from denaturing gel

GTCGCTCGAGAANNNNNNNNNNNNNNNNNNNGGCCAGAGGGCCNNNNNNNNNNNNNNNNNNNTTCTCGAGCCGAC (SEQ ID NO: 58)

3. Prime reverse-strand production with sequence GTCGCTCGAGAA (SEQ ID NO: 59)

GTCGCTCGAGAANNNNNNNNNNNNNNNNNNNGGCCAGAGGGCCNNNNNNNNNNNNNNNNNNNTTCTCGAGCCGAC (SEQ ID NO: 58)
                                                                    ← AAGAGCTCGCTG (SEQ ID NO: 59)

4. Digest with Xho1

TCGAGAANNNNNNNNNNNNNNNNNNNGGCCAGAGGGCCNNNNNNNNNNNNNNNNNNNTTC (SEQ ID NO: 60)
CTTNNNNNNNNNNNNNNNNNNNCCGGTCTCCCGGNNNNNNNNNNNNNNNNNNNAAGAGCT (SEQ ID NO: 61)

4. Clone into U6 expression vector

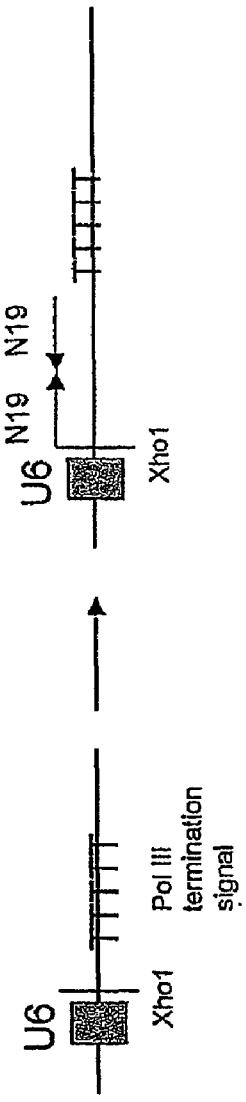

Method 5--Adaptation of cDNA libraries into siRNA libraries
Method uses the E3L gene of vaccinia to prevent cell death in the presence of long double-stranded RNA (ds-RNA)

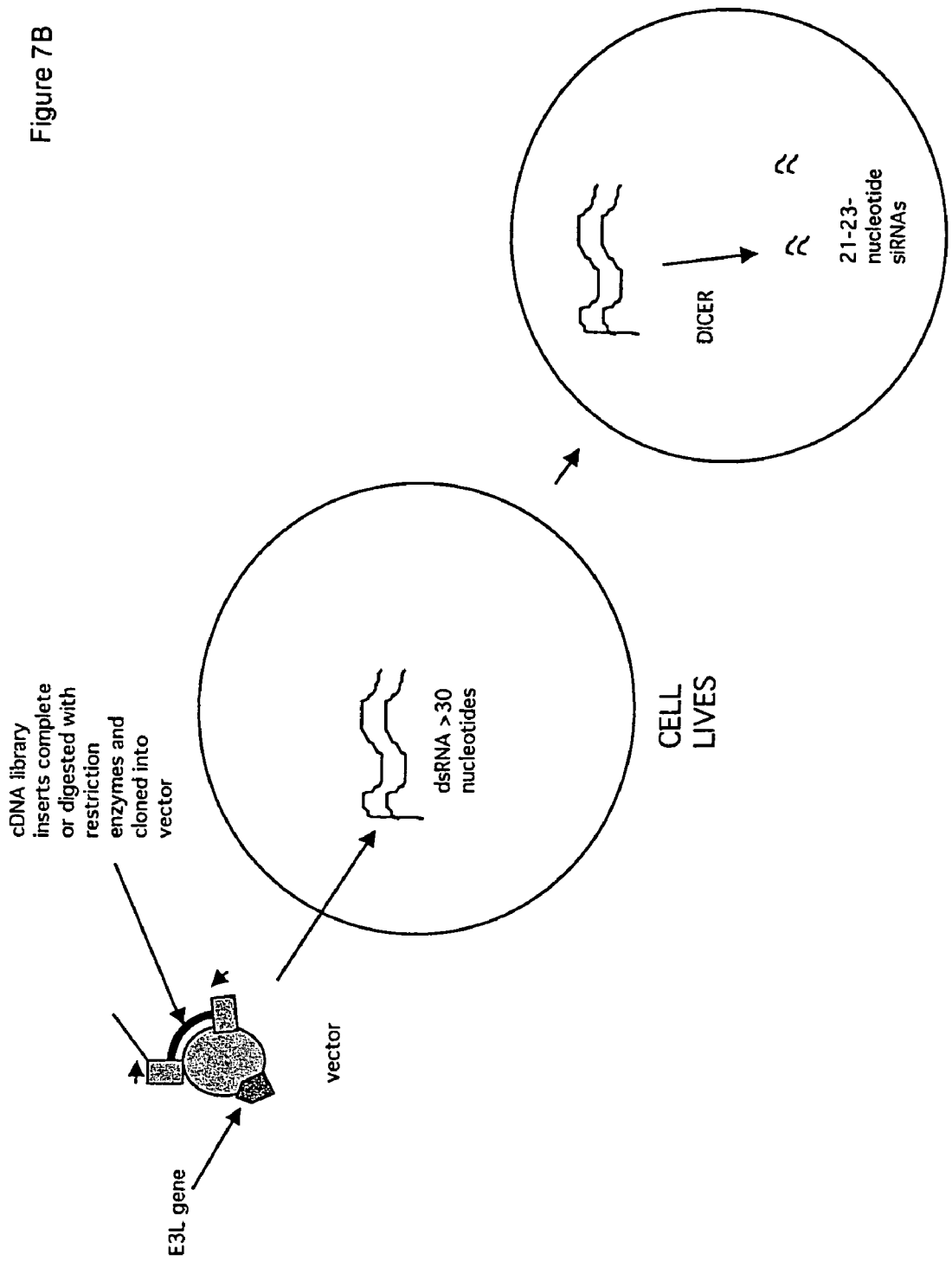

SEQUENCE LISTING

<160> NUMBER OF SEQ ID NOS: 50

<210> SEQ ID NO 1
<211> LENGTH: 10
<212> TYPE: DNA
<213> ORGANISM: Artificial Sequence
<220> FEATURE:
<223> OTHER INFORMATION: Terminator of T7 Transcription

<400> SEQUENCE: 1
catctgtttt                                                          10

<210> SEQ ID NO 2
<211> LENGTH: 19
<212> TYPE: DNA
<213> ORGANISM: Artificial Sequence
<220> FEATURE:
<223> OTHER INFORMATION: T7 Promoter

<400> SEQUENCE: 2
taatacgact cactatagg                                                19

<210> SEQ ID NO 3
<211> LENGTH: 9
<212> TYPE: DNA
<213> ORGANISM: Artificial Sequence
<220> FEATURE:
<223> OTHER INFORMATION: Terminator of T7 Transcription

<400> SEQUENCE: 3 catctgttt                                                           9

<210> SEQ ID NO 4
<211> LENGTH: 46
<212> TYPE: DNA
<213> ORGANISM: Artificial Sequence
<220> FEATURE:
<223> OTHER INFORMATION: Sequence from Library Encoding Shrna

<400> SEQUENCE: 4
aggcgtaacc ccattagttt ctgcagaaac taatggggtt acgcct                  46

<210> SEQ ID NO 5
<211> LENGTH: 46
<212> TYPE: DNA
<213> ORGANISM: Artificial Sequence
<220> FEATURE:
<223> OTHER INFORMATION: Sequence from Library Encoding Shrna

<400> SEQUENCE: 5
tcagggtttt acgtattgtg ctgcagcaca atacgtaaaa ccctga                  46

<210> SEQ ID NO 6
<211> LENGTH: 46
<212> TYPE: DNA
<213> ORGANISM: Artificial Sequence
<220> FEATURE:
<223> OTHER INFORMATION: Sequence from Library Encoding Shrna

<400> SEQUENCE: 6
tgaccggcag caataggagg ctgcagcctc ctattgctgc cggtca                  46

<210> SEQ ID NO 7
<211> LENGTH: 46

```
<212> TYPE: DNA
<213> ORGANISM: Artificial Sequence
<220> FEATURE:
<223> OTHER INFORMATION: Sequence from Library Encoding shRNA

<400> SEQUENCE: 7
tgtttggggg ggtggctacg ctgcagcgta gccaccccccc caaaca                    46

<210> SEQ ID NO 8
<211> LENGTH: 46
<212> TYPE: DNA
<213> ORGANISM: Artificial Sequence
<220> FEATURE:
<223> OTHER INFORMATION: Sequence from Library Encoding shRNA

<400> SEQUENCE: 8
aagtgcgact aaggccgtaa ctgcagttac ggccttagtc gcactt                     46

<210> SEQ ID NO 9
<211> LENGTH: 46
<212> TYPE: DNA
<213> ORGANISM: Artificial Sequence
<220> FEATURE:
<223> OTHER INFORMATION: Sequence from Library Encoding shRNA

<400> SEQUENCE: 9
agctaggtgg gggtcgctgg ctgcagccag cgaccccccac ctagct                    46

<210> SEQ ID NO 10
<211> LENGTH: 46
<212> TYPE: DNA
<213> ORGANISM: Artificial Sequence
<220> FEATURE:
<223> OTHER INFORMATION: Sequence from Library Encoding shRNA

<400> SEQUENCE: 10
gaggggaggc cctcgctggg ctgcagccca gcgagggcct cccctc                     46

<210> SEQ ID NO 11
<211> LENGTH: 46
<212> TYPE: DNA
<213> ORGANISM: Artificial Sequence
<220> FEATURE:
<223> OTHER INFORMATION: Sequence from Library Encoding shRNA

<400> SEQUENCE: 11
aacagtcggt gctcaggcgg ctgcagccgc ctgagcaccg actgtt                     46

<210> SEQ ID NO 12
<211> LENGTH: 46
<212> TYPE: DNA
<213> ORGANISM: Artificial Sequence
<220> FEATURE:
<223> OTHER INFORMATION: Sequence from Library Encoding shRNA

<400> SEQUENCE: 12
ggatagaggg aggtcgcgaa ctgcagttcg cgacctccct ctatcc                     46

<210> SEQ ID NO 13
<211> LENGTH: 12
<212> TYPE: DNA
<213> ORGANISM: Artificial Sequence
<220> FEATURE:
<223> OTHER INFORMATION: Primer

<400> SEQUENCE: 13
```
gtcgctcgag aa                                                              12

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
caccgaggag aagcatgaat tcc                                                  23

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cgttgtaaaa cgacggccag                                                      20

<210> SEQ ID NO 16
<211> LENGTH: 35
<212> TYPE: DNA
<213> ORGANISM: Artificial Sequence
<220> FEATURE:
<223> OTHER INFORMATION: Adapter Oligonucleotide

<400> SEQUENCE: 16
tcgacgcgtg actcgagtcg gatccgcggc cgcat                                     35

<210> SEQ ID NO 17
<211> LENGTH: 32
<212> TYPE: DNA
<213> ORGANISM: Artificial Sequence
<220> FEATURE:
<223> OTHER INFORMATION: Adapter Oligonucleotide

<400> SEQUENCE: 17
gcgactgagc tcagcctagg cgccggcgta gc                                        32

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
gagagcggcc gcgtcctttc cacaagatat                                           30

<210> SEQ ID NO 19
<211> LENGTH: 31
<212> TYPE: DNA
<213> ORGANISM: Artificial Sequence
<220> FEATURE:
<223> OTHER INFORMATION: Primer

<400> SEQUENCE: 19
gcgccatcga taaggtcggg caggaagagg g                                         31

<210> SEQ ID NO 20
<211> LENGTH: 26
<212> TYPE: DNA
<213> ORGANISM: Artificial Sequence

```
<220> FEATURE:
<223> OTHER INFORMATION: Primer

<400> SEQUENCE: 20
cacgggatcc accggtcgcc accatg                                          26

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
cagcggatcc tacaggaaca ggtggtggc                                       29

<210> SEQ ID NO 22
<211> LENGTH: 20
<212> TYPE: DNA
<213> ORGANISM: Artificial Sequence
<220> FEATURE:
<223> OTHER INFORMATION: Adapter Oligonucleotide

<400> SEQUENCE: 22
gatccttttt aagcttggat                                                 20

<210> SEQ ID NO 23
<211> LENGTH: 18
<212> TYPE: DNA
<213> ORGANISM: Artificial Sequence
<220> FEATURE:
<223> OTHER INFORMATION: Adapter Oligonucleotide

<400> SEQUENCE: 23
cgatccaagc ttaaaaag                                                   18

<210> SEQ ID NO 24
<211> LENGTH: 29
<212> TYPE: DNA
<213> ORGANISM: Artificial Sequence
<220> FEATURE:
<223> OTHER INFORMATION: Adapter Oligonucleotide

<400> SEQUENCE: 24
gatccttttt tatcgataaa cctcgagta                                       29

<210> SEQ ID NO 25
<211> LENGTH: 29
<212> TYPE: DNA
<213> ORGANISM: Artificial Sequence
<220> FEATURE:
<223> OTHER INFORMATION: Adapter Oligonucleotide

<400> SEQUENCE: 25
agcttactcg aggtttatcg ataaaaaag                                       29

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
gcgccaagct taaggtcggg caggaagagg g                                    31
```

<210> SEQ ID NO 27
<211> LENGTH: 47
<212> TYPE: DNA
<213> ORGANISM: Artificial Sequence
<220> FEATURE:
<223> OTHER INFORMATION: Primer

<400> SEQUENCE: 27
ggcctcgagc tgccgaagcg agcacggtgt ttcgtccttt ccacaag                47

<210> SEQ ID NO 28
<211> LENGTH: 50
<212> TYPE: DNA
<213> ORGANISM: Artificial Sequence
<220> FEATURE:
<223> OTHER INFORMATION: Oligonucleotide for Generating Random Insert
<220> FEATURE:
<221> NAME/KEY: misc_feature
<222> LOCATION: (11)..(30)
<223> OTHER INFORMATION: n is a, c, g, or t

<400> SEQUENCE: 28
cttgagatct nnnnnnnnnn nnnnnnnnnn ctcgagtgta cacatggcga             50

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide for Generating Insert

<400> SEQUENCE: 29
tcgccatgtg tacactcgag                                              20

<210> SEQ ID NO 30
<211> LENGTH: 20
<212> TYPE: DNA
<213> ORGANISM: Artificial Sequence
<220> FEATURE:
<223> OTHER INFORMATION: Sequence from Library

<400> SEQUENCE: 30
atttctaaag gcgtgtccga                                              20

<210> SEQ ID NO 31
<211> LENGTH: 20
<212> TYPE: DNA
<213> ORGANISM: Artificial Sequence
<220> FEATURE:
<223> OTHER INFORMATION: Sequence from Library

<400> SEQUENCE: 31
cctcttggac tgatacagct                                              20

<210> SEQ ID NO 32
<211> LENGTH: 20
<212> TYPE: DNA
<213> ORGANISM: Artificial Sequence
<220> FEATURE:
<223> OTHER INFORMATION: Sequence from Library

<400> SEQUENCE: 32
gatgttcgag ccagaggtct                                              20

<210> SEQ ID NO 33
<211> LENGTH: 20

```
<212> TYPE: DNA
<213> ORGANISM: Artificial Sequence
<220> FEATURE:
<223> OTHER INFORMATION: Sequence from Library

<400> SEQUENCE: 33
cctcagtgag gccaattgag                                              20

<210> SEQ ID NO 34
<211> LENGTH: 20
<212> TYPE: DNA
<213> ORGANISM: Artificial Sequence
<220> FEATURE:
<223> OTHER INFORMATION: Sequence from Library

<400> SEQUENCE: 34
gttcttgtct taaacggagg                                              20

<210> SEQ ID NO 35
<211> LENGTH: 20
<212> TYPE: DNA
<213> ORGANISM: Artificial Sequence
<220> FEATURE:
<223> OTHER INFORMATION: Sequence from Library

<400> SEQUENCE: 35
atccgcttgt aatctacagg                                              20

<210> SEQ ID NO 36
<211> LENGTH: 20
<212> TYPE: DNA
<213> ORGANISM: Artificial Sequence
<220> FEATURE:
<223> OTHER INFORMATION: Sequence from Library

<400> SEQUENCE: 36
tcacttttat ggggtcatta                                              20

<210> SEQ ID NO 37
<211> LENGTH: 20
<212> TYPE: DNA
<213> ORGANISM: Artificial Sequence
<220> FEATURE:
<223> OTHER INFORMATION: Sequence from Library

<400> SEQUENCE: 37
cggtttgcaa ttgcaagcat                                              20

<210> SEQ ID NO 38
<211> LENGTH: 20
<212> TYPE: DNA
<213> ORGANISM: Artificial Sequence
<220> FEATURE:
<223> OTHER INFORMATION: Sequence from Library

<400> SEQUENCE: 38
ctttcgaggc agggctctga                                              20

<210> SEQ ID NO 39
<211> LENGTH: 20
<212> TYPE: DNA
<213> ORGANISM: Artificial Sequence
<220> FEATURE:
<223> OTHER INFORMATION: Sequence from Library

<400> SEQUENCE: 39
```

-continued acacctctgc tgatcaaatt                                               20

<210> SEQ ID NO 40
<211> LENGTH: 20
<212> TYPE: DNA
<213> ORGANISM: Artificial Sequence
<220> FEATURE:
<223> OTHER INFORMATION: Sequence from Library

<400> SEQUENCE: 40
tatgcggcgt tcagaccgca                                               20

<210> SEQ ID NO 41
<211> LENGTH: 20
<212> TYPE: DNA
<213> ORGANISM: Artificial Sequence
<220> FEATURE:
<223> OTHER INFORMATION: Sequence from Library

<400> SEQUENCE: 41
atcgctgtga cttcatgaca                                               20

<210> SEQ ID NO 42
<211> LENGTH: 20
<212> TYPE: DNA
<213> ORGANISM: Artificial Sequence
<220> FEATURE:
<223> OTHER INFORMATION: Sequence from Library

<400> SEQUENCE: 42
taacaaatgc gctacgtcct                                               20

<210> SEQ ID NO 43
<211> LENGTH: 20
<212> TYPE: DNA
<213> ORGANISM: Artificial Sequence
<220> FEATURE:
<223> OTHER INFORMATION: Sequence from Library

<400> SEQUENCE: 43
atcaggcgga gtatagtttc                                               20

<210> SEQ ID NO 44
<211> LENGTH: 20
<212> TYPE: DNA
<213> ORGANISM: Artificial Sequence
<220> FEATURE:
<223> OTHER INFORMATION: Sequence from Library

<400> SEQUENCE: 44
agtacctttt gcgcctctcc                                               20

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide Derived from Human Estrogen
      Receptor Alpha

<400> SEQUENCE: 45
aaggccttct tcaagagaag t                                             21

<210> SEQ ID NO 46
<211> LENGTH: 21
<212> TYPE: DNA

```
<213> ORGANISM: Artificial Sequence
<220> FEATURE:
<223> OTHER INFORMATION: Oligonucleotide Derived from Human Estrogen
      Receptor Alpha

<400> SEQUENCE: 46
aagatcacag acactttgat c                                            21

<210> SEQ ID NO 47
<211> LENGTH: 49
<212> TYPE: DNA
<213> ORGANISM: Artificial Sequence
<220> FEATURE:
<223> OTHER INFORMATION: Encodes shRNA Directed Against Human Estrogen
      Receptor Alpha

<400> SEQUENCE: 47
aaggccttct tcaagagaag tggtaaccac ttctcttgaa gaaggcctt              49

<210> SEQ ID NO 48
<211> LENGTH: 49
<212> TYPE: DNA
<213> ORGANISM: Artificial Sequence
<220> FEATURE:
<223> OTHER INFORMATION: Encodes shRNA Directed Against Human Estrogen
      Receptor Alpha

<400> SEQUENCE: 48
aagatcacag acactttgat cggtaaccga tcaaagtgtc tgtgatctt              49

<210> SEQ ID NO 49
<211> LENGTH: 21
<212> TYPE: RNA
<213> ORGANISM: Artificial Sequence
<220> FEATURE:
<223> OTHER INFORMATION: RNA Directed Against Human Estrogen
      Receptor Alpha

<400> SEQUENCE: 49
aaggccuucu ucaagagaag u                                            21

<210> SEQ ID NO 50
<211> LENGTH: 20
<212> TYPE: RNA
<213> ORGANISM: Artificial Sequence
<220> FEATURE:
<223> OTHER INFORMATION: RNA Directed Against Human Estrogen Receptor
      Alpha

<400> SEQUENCE: 50
agaucacaga cacuuugauc                                              20
```

SMALL INTERFERING RNA LIBRARIES AND METHODS OF SYNTHESIS AND USE

CROSS REFERENCE TO RELATED APPLICATIONS

This application claims priority to U.S. Provisional Patent Application 60/469,169, filed on May 9, 2003, the entirety of which is incorporated herein by reference.

FIELD OF THE INVENTION

This invention pertains to small interfering RNA (siRNA) libraries, particularly random or semirandom siRNA libraries, methods for preparing such libraries and methods for using such libraries.

BACKGROUND OF THE INVENTION

Small interfering RNAs (siRNAs) are double stranded RNAs that specifically destroy any RNA within a cell containing a matching sequence. In this manner, siRNAs are effective suppressors of various genes, including oncogenes and tumor suppressor genes via a phenomenon known as RNA interference (RNAi). RNA interference disrupts gene expression via a cellular system utilizing double-stranded RNAs. Recognition of this phenomenon was initially identified in *Caenorhabditis elegans* (see, e.g., Fire et al., *Nature* 391, 806-811 (1998)). More recently, 21 or 22 nucleotide double stranded RNAs with 2-nucleotide 3' overhangs have been reported to show RNAi activity in mammalian cells (see, e.g., Elbashir et al., *Nature* 411, 494-98 (2001) and Caplen et al., *Proc. Natl. Acad. Sci. USA* 98, 9742-47 (2001)). Miyagishi et al. described the construction of a siRNA expression vector employing two U6 RNA Polymerase III promoters separately driving transcription of either a sense or an antisense version of a short DNA sequence. After transcription, a siRNA was derived from duplex formation between the sense and antisense strands of the RNA transcripts. (see Miyagishi et al., *Nature Biotech.* 19, 497-500 (2002)). Brummelkamp et al. constructed a mammalian expression vector using a polymerase-III H1-RNA gene promoter linked to a gene-specific insert of 19 nucleotides (sense) separated by a short spacer sequence from the antisense sequence of the same 19 nucleotide gene-specific insert. The complementary nature of the resulting RNA caused the transcripts to form a 19-base pair stem-loop structure (see, Brummelkamp et al., *Science*, 296, 550-553 (2002)).

RNAi could serve as a powerful tool for functional genomics. For example, Kamath et al. described an interfering RNA system for attempting phenotypic identification of genes in *C. elegans* (see, Kamath et al., *Nature* 421, 231-237 (2003)). Their particular approach used double stranded RNA sequences hundreds of base pairs long. This approach, however, would not be suitable for application in higher organisms, such as mammalian systems, in which double-stranded RNA's over 30 base pairs in length induce a host defense response via the interferon pathway which nonspecifically inhibits mRNA and protein translation. Because the system described by Kamath et al. used substantially longer double-stranded RNA, it would not be suitable for use in mammalian cells. Additionally, the system of Kamath et al. was not generated from random combinations of nucleotides and thus would not be broadly applicable for functional genomics applications.

For functional genomics of higher organisms, a set of short double-stranded RNAs, 12-25 nucleotides in length would be useful. Double-stranded RNAs of this length do not induce a host defense response. Optimally, functional genomics requires a large set of siRNAs, each with a unique sequence such that all the genes of an organism are statistically represented by at least one siRNA. Such a "siRNA library" (i.e., comprising a random or semirandom set of siRNAs) could facilitate the identification of specific genes or viruses responsible for resulting phenotypes in higher organisms, such as mammalian cells.

The desirability of siRNA libraries for drug discovery and disease modification has prompted two recent approaches to library construction. The first "brute force" approach uses traditional methods to generate siRNA sequences directed against one gene at a time and pools these to form an siRNA library (Boutros, M, et al, *Science*, 303(5659):832-35. (2004), Paddison, P J et al, *Nature;* 428(6981):427-31 (2004)). The second approach derives siRNA libraries from pooled cDNA's by using the enzyme MmeI to digest cDNAs into 20-bp templates for siRNA (Sen et al., *Nat Genet.;* 36(2): 183-89 (2004); Shirane et al., *Nat Genet.;* 36(2): 190-96 (2004)).

The "brute force" method of generating siRNA libraries has a number of limitations. There is a tremendous workload involved in this approach, and such libraries have only been reported for a few organisms. In addition, there are numerous gaps expected in both "brute-force" and cDNA-derived libraries for several reasons. Firstly, such libraries attenuate only coding RNA. It should be noted that coding RNAs used in these approaches comprise roughly 4% of the genome. It is increasingly recognized that noncoding RNAs play important functional roles in the cell, including regulation of pathways and sequestration of proteins. For example, the noncoding RNA SCA8 has been shown to cause neurodegeneration (Mutsuddi, M. et. al., *Curr. Biol.,* 14, 302-08 (2004)). All functional noncoding RNAs will be missed both by directed ("brute-strength") libraries and libraries derived from cDNAs. Secondly, siRNAs can trigger heterochromatin formation of specific areas of genomic DNA, resulting in promoter silencing and possibly other effects (Volpe et al., *Science;* 297(5588):1833-37 (2002)). Any such genomic effects, which could be quite durable, will be missed both by directed ("brute-strength") libraries and libraries derived from cDNAs. Thirdly, directed ("brute-strength") libraries and libraries derived from cDNAs are not well-suited to attenuate genes of tissues and organisms besides those they were designed for. Thus, for example, such libraries will be of little use in attenuating genes of emerging and unknown viruses. Fourthly, an additional limitation of brute-force cloning to generate siRNA libraries is that this approach is likely to collect sequences that are over 75% suppressive. Some phenotypes shift when a protein is attenuated by 50% and shift again when the protein is even more seriously suppressed (see, e.g., Muraoka R S Mol Cell Biol. 2002 April; 22(7): 2204-19.). A fifth limitation of these approaches is that neither are very efficient. For example, the brute force approach is extremely time intensive and will contain holes related to splice variants. Key physiologic genes (e.g., p53, p73, Cyclins) are expressed in many spliced forms that vary in their function. Some spliced forms have opposing effects to each other. Interfering RNA which targets all splice variants of a gene may not have a large effect if it decreases both positive and negative acting splice forms. A sixth major drawback to cDNA-based libraries is that they contain vast overrepresentation of siRNA or shRNAs directed against common messages, whereas many of the most interesting target genes (e.g. transcriptional regulators, phosphatases) are expressed at low levels.

Each of the limitations of directed "brute-strength" libraries and cDNA-based libraries could be addressed by a library that is comprised of random siRNA sequences. However, the synthesis of random siRNAs is not well established, and the construction of a random siRNA library heretofore has not been demonstrated. Frustrating the creation of a siRNA library has been the difficulty in joining random DNA oligomers with unknown sequences to their exact complementary sequences wherein the production of such constructs is sufficient to cover all combinations of nucleotides in oligomers of a desired length. The necessary formation of double stranded RNA duplexes from the template DNA oligomers is an additional hurdle to overcome.

Miyagashi et al. (*Nature Biotech.*, 19, 497-500 (2002)) speculated that an opposing U6 promoter system may allow the production of randomized siRNA libraries. However, the Miyagashi report does not disclose the construction of any such library, nor does it disclose any additional technical features or provide any instruction concerning the construction of such a library.

United States Patent Application Publication 20040005593 (Lorens) speculates that random libraries of interfering RNA molecules may be constructed by synthesizing a pool of oligonucleotides comprising a restriction site, a randomized siRNA sequence, a complementarity region sequence, and a hairpin-forming linker sequence (optionally a U-turn motif, a ribozyme and/or or a two complementary sequences that form a hairpin or stem loop structure). According to the published Lorens application, the oligonucleotides will adopt a hairpin structure, which will function as a substrate for a DNA polymerase, facilitating the synthesis of a complement sequence of the randomized siRNA sequence. According to the published Lorens application, the hairpin structure is then denatured and hybridized to a primer at the 3' end allowing the conversion of the total sequence to double stranded DNA by a DNA polymerase. The double stranded oligonucleotides, supposedly encoding a random assortment of siRNA sequences, then are cloned into a retroviral vector to generate an siRNA-expression vector library. The published Lorens application, however, does not disclose the construction of any random siRNA library. Moreover, the approach proposed by Lorens would not result in a random library. A technical hurdle to the successful application of the Lorens approach is that the hairpin structure has great homology to itself and will tend to self-anneal. Thus, it will be necessary to use an amount of primer in great excess of the template to facilitate complementary strand priming, which is not taught by Lorens. Another consequence of the high self-homology of the hairpin structure is that self-annealing actually leads to a non-random library if the approach disclosed by Lorens is followed. Self-annealing of the hairpin structure will prevent polymerization of the complementary strand. Unless such polymerization occurs under conditions that prevent self-annealing, regions rich in GC content are more likely to self-anneal than are regions rich in AT content; hence, GC-rich sequences will be selected against in the process. Lorens calls for denaturation of the hairpin prior to polymerization (which is necessary in any event to permit binding of the primer); however, Lorens does not specify that the polymerization occur under conditions that maintains the denaturation of the hairpin structure. Accordingly, the distribution of sequences in the library produced by the Lorens approach will be non-random with respect to GC-rich vis-à-vis non-GC-rich sequences.

In light of the deficiencies with existing technology, new synthetic methods are needed that can produce random siRNA libraries (including siRNA- and shRNA-encoding libraries). Such methods and the resulting libraries would facilitate a multitude of tasks such as, identification of genes of interest, analysis of gene function and identification of therapeutically useful siRNA sequences.

BRIEF SUMMARY OF THE INVENTION

In one aspect, the invention provides a random siRNA (encoding) library. Another aspect of the invention is a method for construction of siRNA libraries. The method involves producing a population of random oligodeoxyribonucleotides, which can be cloned into vectors containing site-specific recombinase sites for generating inverted repeats of that random sequence [sense-antisense] in suitable host cells, and then cloned into expression vectors with RNA polymerase promoters to generate complementary stem-loop RNAs when they anneal. The random hairpin [sense-antisense] sequences can either be cloned singly into vectors or as multiple, tandem inserts. Alternatively, the random sequence can be engineered to anneal for self-priming polymerase reactions that generate the stem-loop, followed by cloning into the expression vector. In another aspect, an siRNA library can be produced by either digesting a cDNA library and cloning the digests into plasmids such that they are flanked by two opposing RNA polymerase promoters, or by cloning a random oligonucleotide library between the two RNA polymerase promoters.

In another aspect, the invention provides a method of using a siRNA library, for example, to identify candidate genes that mediate phenotypes of interest. The siRNA library is introduced into a population of cells. The population of cells then is subjected to a selection process to select a subpopulation of cells exhibiting a different behavioral, biochemical, chemical, functional, molecular, morphological, phenotypic, or physical property from the remainder of population. Following the selection process, the subpopulation (i.e., subset) of cells can be isolated, analyzed, and/or cloned as desired. Such analysis of the subpopulation can be identification of the siRNA species responsible for the different properties of the subpopulation relative to the remainder of the population. Alternatively, the subpopulation can be further analyzed by genomic, proteomic, and/or cellomic assays. Where such genomic, proteomic, and/or cellomic assays are employed, the method can produce several useful bioinformatics products.

The siRNA library described by this invention will be useful in rapid functional identification of critical genes involved in cancer, cell differentiation, viral infection, bacterial pathogenesis, metabolic pathways, signal transduction pathways, lytic pathways, as well as other research fields relying on phenotypic analysis. Specific siRNAs identified through this process may have direct therapeutic value.

Another aspect of the invention is vector systems for use in constructing siRNA libraries and/or that can express single siRNAs and siRNA libraries both constitutively and in an inducible fashion.

These aspects and advantages of the invention, as well as additional inventive features, will be further apparent from the accompanying figures and upon reading the following detailed description.

DESCRIPTION OF THE FIGURES

FIGS. 1A-1C illustrate a method for generating DNA hairpins and a random siRNA library.

FIG. 3 illustrates a method for regulating expression of a random siRNA library using inducible T7 polymerase.

FIGS. 4A and 4B illustrates a method for constructing a random siRNA library employing a bidirectional approach using PolIII promoters.

FIG. 5 illustrates a method for constructing a random siRNA library employing a bidirectional approach using the T7 promoter.

FIGS. 6A and 6B illustrate a method for generating a random siRNA library using a self-annealing hairpin.

FIGS. 7A and 7B illustrate a method of adapting cDNA libraries into siRNA libraries.

DETAILED DESCRIPTION OF THE INVENTION

Figure 1C:
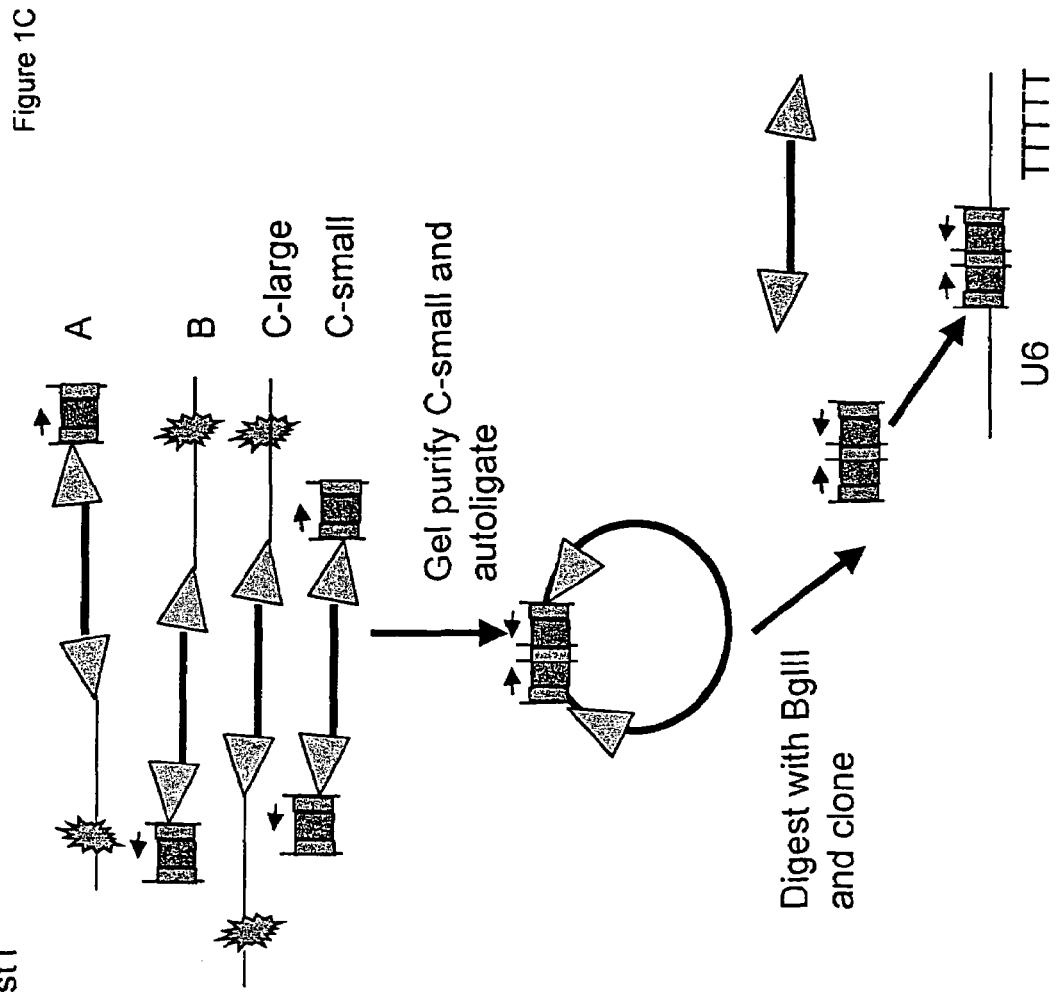

In the context of the present invention, an "siRNA" (small interfering RNA) is a species of RNA that has a double stranded structure and wherein each strand is between about 12 and about 35 nucleotides in length. An siRNA can either comprise two separate strands that bind solely through complement base-pairing, or an siRNA can be a single strand with a loop between the sense and antisense sequence. These fold together to make a hairpin loop, or short hairpin RNA (shRNA), which is processed within cells to make purely double-stranded siRNA.

One aspect of the invention is a random or semirandom siRNA library. In this context an "siRNA library" is a collection of distinct sequences that comprise or encode siRNA or shRNA. Thus, the library can comprise either DNA or RNA. An example of an siRNA library comprising DNA is a library of DNA-based expression vectors (e.g., plasmids, viruses, etc.), which contain distinct sequences encoding siRNA or shRNA. The DNA vectors produce the siRNA or shRNA when introduced into a suitable environment for transcribing the DNA sequences within the vectors (such as a cellular or bacterial system or a suitable in vitro transcription environment). Within a cell, in turn, each shRNA is processed to siRNA. Another example of a siRNA library comprising DNA is a population of cells that contain DNA-based expression vectors, which contain distinct sequences encoding shRNA. An example of an siRNA library comprising RNA is a collection of distinct siRNA or shRNA species.

The inventive library is a collection of siRNAs or shRNAs having random or semirandom sequences (or, as noted, DNA encoding such sequences). While the library can be semirandom, a truly random siRNA or shRNA library is most desirable, as it can contain all possible sequences in equal proportion. Also, for use as genomics reagents in cells of higher organisms (or cell lines derived from higher organisms), it is highly desirable for the RNAs within the library to be short enough to evade the cellular host defense system, yet, the siRNAs should be long enough to form the sense-loop-antisense structure and have activity against complementary RNA species within cells. Thus, preferably, the siRNAs or shRNAs within the library have a random sense sequence of greater than about 10, such as between about 12 and about 35 nucleotides, or between about 15 and about 30 nucleotides, more typically between about 17 and about 23 nucleotides, and 19-mer or 20-mer sequences are the most typical.

A random siRNA or shRNA library can be used to attenuate low-expressed or rare targets with probability substantially equal to that with which it attenuates high targets (such as actin). A random library contains or encodes siRNAs or shRNAs for generating a graded response that is selectable by phenotype. Random siRNA or shRNA libraries contain splice-form specific RNAi sequences, as well as sequences which can target genomic DNA sequences (e.g., both coding and noncoding DNA). A truly random library contains siRNA-coding or shRNA-coding sequences directed against unknown sequences, such as those found in emerging diseases, unknown viruses, or artificial mutants. Accordingly, the inventive random or semirandom siRNA or shRNA library is particularly useful for modulating the expression of sequences in such potential threats to health and safety. The completeness of the random library also facilitates its use in diverse tissues, species and in the setting of genetic variants.

The random or semirandom siRNA or shRNA library can be made in accordance with any suitable method. However, another aspect of the invention provides a method for preparing a siRNA or shRNA library.

In accordance with one embodiment of the inventive method, first a population of oligodeoxyribonucleotides (oligoDNAs) is synthesized, which have, as at least a portion of their sequence, the aforementioned random or semirandom nucleotides. Any suitable method can be employed for generating the population of oligoDNAs (e.g., polymerase chain reaction (PCR), reverse transcription of an RNA library, isolation of DNA fragments from an organism, any other means of nucleotide polymerization). However, a preferred method involves employing standard oligoDNA synthetic machinery, which can produce a population of random or semirandom sequences by employing a stochastically random mixture of the four nucleotides during synthesis.

While the initial population of oligoDNAs contains the random or semirandom sequence, the entirety of the initial oligoDNAs need not be random or semirandom. Indeed, in one preferred embodiment, the random or semirandom sequence is flanked by preselected 5' and 3' restriction enzyme sites. In this embodiment, the restriction enzyme sites flanking the random or semirandom sequence can be the same or different, but to facilitate manipulation of the construct following cloning, it is preferred that the 3' restriction site is different than the 5' restriction site. Also, it is preferred that such restriction enzyme recognition sites contain at least 6, and more preferably 8 nucleotides, as this reduces the likelihood that the random or semirandom oligoDNAs will be lost after subsequent restriction digestion during cloning. Furthermore, it is preferred for the restriction sites to be sticky after digestion and not result in blunt ends, as this facilitates ready ligation of complementary ends during cloning. Preferred restriction sites for engineering into the 3' and 5' ends of the oligoDNAs include AscI, FseI, BglII, BstEII, PstI, NotI, and EagI, but those of skill in the art will appreciate that other sites can be suitably employed.

Such a population of oligoDNAs engineered to contain 5' and 3' restriction sites flanking the random or semirandom sequence can be cloned into a suitable vector for constructing the mature sense-spacer-antisense sequence. Typically, prior to insertion into the vector, the population of single stranded oligoDNAs is primed. The oligoDNAs are bounded by restriction sites and followed by a priming sequence. Preferably, the random sequence is between about 15 and about 30 nucleotides, and most preferably is about 20 nucleotides. The priming sequence is preferably at least about 5 nucleotides. The complementary strand synthesized by standard methodology.

In a preferred embodiment, the oligoDNAs can be cloned into plasmids having two recombinase binding sites for a site-specific recombinase, in which the central spacer sequence within each recombinase binding site is in opposite orientation relative to the other site. Such recombinase sites can be, for example, two FRTs (which are recognized by the FLP recombinase), or two loxp sites (which are recognized by the cre recombinase) or any other suitable recombinase and its recognition sequence, several of which are known in the art (Sadowski, P D. 1995, Prog Nucleic Acid Res Mol Biol 51:53-91). The oligoDNAs are cloned into a plasmid system between two such opposite-orientation recombinase sites, because such orientation is required to generate the sense-spacer-antisense constructs, by producing an inverted repeat of the sequence between the sites. More preferably, the oligoDNAs are introduced into such a plasmid such that the restriction sites within the oligoDNAs are between yet near to one of the two recombinase recognition sequences, such that it is asymmetrically placed between the FRTs [eg. 90%: 10%] [see Method 1A—FIGS. 1A-1C].

After such plasmids containing the dual recombinase site—oligoDNAs cassettes are created, the population of plasmids is introduced into a population of host cells that produce the appropriate recombinase enzyme for the particular recombinase recognition sites present in the plasmids. Desirably, such host cells are bacteria, but they can be other cells that are readily grown in culture (e.g., yeast, transformed cell lines, etc.). Moreover, it is desirable for the host cell population to express the recombinase enzyme, and in one approach, the host cell population inducibly expresses the desired recombinase enzyme. In a preferred embodiment, the plasmid that is used for the oligoDNA also is engineered to inducibly express the recombinase (e.g., FLP) in bacteria [e.g. *E. coli*]. The plasmid can express the recombinase either in a constitutive or inducible manner and obviates the need for the host cell to code for the appropriate recombinase enzyme. Transformation of host cells with the plasmid constructs can be achieved by any suitable manner known in the art, such as, for example, electroporation, lipofection, calcium-phosphate mediated methods, DEAE-dextran mediated methods, calcium chloride mediated methods, the Hanahan method, the Inoue method, chemical treatment mediated methods and other known techniques in the art. However, it is desirable for the plasmids to be transfected into the host cells at a ratio that reduces the likelihood that more than one plasmid will enter a single host cell. Preferably, the plasmid construct is transformed into the host cells at a ratio of about 1:1 (plasmid:cells).

Because the average mammalian gene is roughly 2400 nt in length, the entire library can contain redundant sequences targeting a given gene (e.g, the entire library would target each gene at roughly 2400 overlapping sites). Since an adenine is preferred at the first or second nucleotide in the messenger RNA sequence which is targeted by the siRNA end, it is estimated that ½ of random siRNA sequences will be optimally targeted. It has been estimated that ¼ of siRNA sequences are highly effective. Therefore, in some embodiments, a bacterial transformation of about $5\times10^9$ (well within current bacterial competency levels) may generate a library that is effective against all genes.

The plasmids then are incubated within the bacterial host cells such that the plasmids are replicated and exposed to the recombinase. In the presence of the recombinase, site-specific recombination occurs between the opposite orientation recombinase recognition sites within a given cell in the population of host cells to invert the sequence between the sites. Recombination yields a mixed population including three types plasmids within a given cell, each of which is derived from an initial plasmid containing the two recombinase sites—oligoDNAs cassette: (a) a plasmid containing the cassette in the same orientation as the original plasmid (A form), (b) a plasmid containing the cassette in antiparallel (i.e., "flipped") orientation (B form), and a plasmid containing merged, yet separated "dual cassettes" resulting from recombination between an A and B form plasmid [see Method 1A, step 4a, FIG. 1B]. These inverted repeats are separated, however, by intervening plasmid sequence. Of course, the plasmid (c) will be twice the size of the plasmids (a) and (b), which facilitates isolation by digestion and gel electrophoresis. Thus, following recombinase activity, the plasmid DNA is isolated from the population of host cells, using any suitable technique (e.g., lysis with SDS, alkaline lysis with SDS, boiling lysis, toothpick minipreparation protocols, midipreparation protocols, maxipreparation protocols as well as other techniques known in the art). After isolation, the plasmid DNA is digested with one of the restriction enzymes specific for the 3' restriction site or the 5' restriction site engineered into the initial population of the oligoDNAs to generate a "small" plasmid and a "large" plasmid due to the asymmetric placement of the random oligo DNA between the recombinase sites. This is followed by a gel separation and isolation. [Method 1A, step 5a FIG. 1C and FIGS. 10A and 10B]. Because each repeat was flanked by a unique restriction site on one side and another restriction site on the other, a smaller fragment containing both inverted repeats is isolated using one of the enzymes (e.g. PstI), and this fragment can then be autoligated (i.e. closed on itself) to make the inverted repeats contiguous.

Within the resulting ligated plasmids, the inverted random cassettes desirably are digested with a restriction endonuclease specific for the second of the two restriction sites present in the initial oligoDNAs (e.g. BglII). This will cleave on each side of the sense and antisense random or semirandom sequence. Following the digestion, the small DNA fragments encode siRNA and can be cloned into an appropriate RNA expression vector to make an siRNA encoding cassette. Each of the siRNA-encoding cassettes includes a sense random sequence and a complementary antisense sequence separated by a spacer derived from either the 3' or the 5' restriction site (i.e., derived from the sticky ends of the internal restriction site) separating the sense and antisense random or semirandom DNA. Depending on the restriction site, the resulting spacer will be between about 4 and about 15 nucleotides, and preferably between about 6 and about 10 nucleotides in length (e.g., about 7 or 8 nucleotides in length). Separation of sense and antisense DNA sequences with a restriction site spacer has been shown to be effective in such expression systems (see, e.g., Devroe et al., *BMC Biotechnology*,. 2, pg. 1-5 (2002)). Also, the dual cassettes (siRNA-encoding cassettes) can be cloned into the plasmids as single inserts or as oligomeric inserts. Such inserts can, for example, comprise between about 2 and about 10 inserts, or from about 10-100 inserts or even between about 100 and about 1000 or more inserts. In some cases, known specific hairpin-coding double-stranded DNAs will be combined in tandem with random and/or other known sequences within the vector in order to target overlapping or non-overlapping genetic or signaling pathways. Thus, the inventive method can further comprise cloning the dual cassettes encoding the random or semirandom siRNA (such as an shRNA) in tandem with one or more cassettes encoding an siRNA (such as an shRNA) having a predefined sequence.

After isolation, the inverted repeat cassettes are cloned into a vector suitable for generating RNA in the target cells for screening. For example, the cassette can be cloned into an RNA expression vector. The cassettes can either be cloned singly or as tandem multimers into the expression vector. Exemplary RNA vectors can most preferably include retroviral vectors, plasmids, adenoviral vectors and lentiviral vectors; however, other suitable RNA expression vectors are known in the art. RNA expression vectors typically contain an RNA polymerase promoter and a transcription termination site (e.g., a polythymidine (TTTTT) termination site or other suitable site), and the inverted repeat cassette is positioned between the promoter and terminator. Such vectors typically are suitable for introduction into the cells of higher organisms to achieve RNA expression within such cells. Preferably, the RNA Polymerase promoter is a RNA Polymerase III promoter and most preferably is a U6 or H1 RNA Polymerase III promoter or a T7 bacteriophage promoter. Also, in some embodiments, it is preferably for the recipient vector to have opposing promoters (such as opposing H1 and/or U6 promoters). In such an embodiment, each promoter can transcribe shRNA from the opposite direction. In another embodiment, the polymerase I or II promoters can be used or multiple tandem promoters including those for any DNA-dependent RNA polymerase could be used. Desirably, the dual cassettes are cloned into such vectors immediately downstream of the RNA promoter and immediately upstream of the termination site (e.g., a polyT site, such as TTTTT).

Figure 2A:
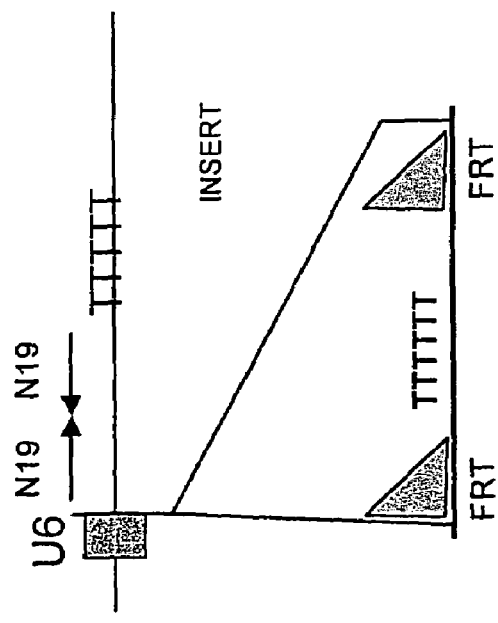
FIGS. 2A-2B illustrate a method for regulating expression of a random siRNA library using inducible FLP recombinase.
Figure 2B:
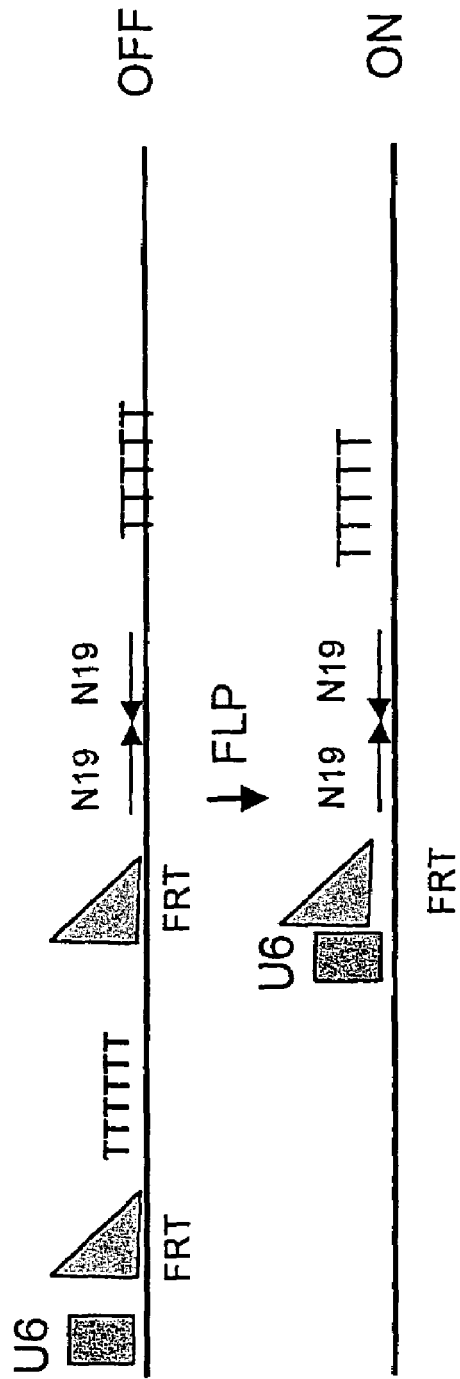

Alternatively, prior to cloning of the final cassettes encoding siRNA, an insert comprising two parallel recombinase sites flanking an RNA polymerase termination signal (i.e., a second termination signal, separate from that in the RNA expression vector 3' of the siRNA encoding sequences) can be introduced between the RNA polymerase promoter and the siRNA encoding sequence. [see Method 1B, FIGS. 2A-2B]. Because the recombinase sites in such an insert are in parallel (i.e., spacer oriented in the same direction), in the presence of the recombinase enzyme, the dual recombinase sites are resolved into a single site, thus excising the termination signal. Accordingly, this variation permits the construction of an inducible siRNA library because the siRNA-encoding vectors will be "off" and unable to transcribe the siRNA sequence until the appropriate recombinase is added. For subsequent use, thus, the library can be activated when in the presence of recombinase.

Where the RNA promoter within the expression vector is aT7 bacteriophage promoter, the termination site most preferably is a CATCTGTTTT (SEQ ID NO:1) terminator of T7 transcription (He et. al., JBC, v273, 18802-11 (1998)) [see Method 1C, FIG. 3]. To ensure efficient expression of the siRNA cassette within mammalian cells, the plasmid containing such cassettes also preferably contains an expression cassette (e.g., suitable for expressing genes in mammalian cells) encoding a protein able to direct transcription from a T7 bacteriophage promoter, such as the T7 protein or a derivative. One preferred derivative is a fusion between the T7 protein (containing at least the DNA-binding and transcriptional activation domains from T7) and a nuclear localization sequence (e.g., from SV40 or another protein) so that it can enter the nucleus to interact with the T7 promoter in the plasmid. This system further facilitates inducible expression of the siRNA library, which can be quite important for use in mammalian cell experiments and ultimately in animal models and human disease treatment. For example, the T7 can be expressed as a fusion protein with the gene coding for amino acids 251-595 of the human estrogen receptor mutant (such as (G521R)) that responds to tamoxifen and not estrogen (Danielian et al, 1993, Mol. Endo. 7: 232-240). A similar fusion with mouse mutant estrogen receptor G525R also can be employed. This results in the T7 polymerase being repressed until tamoxifen is added. Tamoxifen therefore controls expression of the siRNA library. This inducible system is also very useful for the induced control of single siRNAs directed against specific genes, and the invention provides a method of inducibly regulating the expression of T7-driven siRNA using such T7-polymerase-estrogen receptor fusion proteins The RNA expression vectors containing the siRNA expression cassettes represent a population of unique RNA expression cassettes, each of which contains the random or semirandom sequence, which have been pooled to form an siRNA library. The vectors within such population may each contain one unique cassette per vector, or a the vectors may be constructed to contain multiple tandem cassettes in each vector. The library can be expressed by introducing the plasmids containing the library into suitable host cells.

It will be observed that the foregoing provides a method of employing DNA site-specific recombinases (e.g., FLP or Cre) to generate DNA hairpins. As described, where the sequences of the initial population of oligoDNAs are random or semirandom, the resulting hairpin is a random or semirandom siRNA-encoding library. However, the method also can be used to generate DNA hairpins directed to a specific target. Thus, where the initial population of oligoDNAs has a pre-designed sequence, the resulting DNA hairpins are specific siRNA-encoding sequences. It will be understood that, insofar as oligoDNAs can be generated that may be specified except at one or a few nucleotides, so too can the inventive method achieve the construction of DNA hairpins that encode siRNA populations that vary from each other at only one or a few portions of an otherwise common sequence. Such libraries can be said to be a type of semirandom library.

To facilitate this inventive method, the invention also provides a vector suitable for facilitating the generation of DNA hairpins using recombinase. Such a vector is plasmid containing two recombinase recognition sites oriented towards each other and having a sequence of DNA between the two recombinase recognition sites (e.g., Cre or LoxP). The sequence between the two recombinase recognition sites comprises at least one restriction endonuclease recognition sequence (such as, for example, Asc1 or Fse1), and most preferably at least two restriction endonuclease recognition sequences. The two endonuclease recognition sites can be the same or different, but preferably the two restriction endonuclease recognition sequences are not the same sequence. The plasmid also can include an expression cassette encoding a recombinase enzyme (e.g., FLP or CRE) appropriate for recognizing the two recombinase recognition sites in the plasmid. Preferably, this enzyme can be inducibly expressed from the plasmid (e.g., using a temperature-sensitive expression system), which will permit the plasmid to be used in most bacterial strains. Where the plasmid includes such a recombinase expression cassette, preferably, the expression cassette is not between the two restriction endonuclease sequences. The half-hairpin sequences of DNA (from which DNA-hairpins will be generated by this method) are cloned into expression plasmids at the site of the endonuclease recognition sequences. Accordingly, the inventive plasmid also can include a DNA sequence encoding one half of a hairpin-encoding shRNA (random or directed). Generally, where the plasmid includes a DNA half-hairpin sequence, it is between said two restriction endonuclease recognition sequences. An example of such a plasmid is pFRT (See FIG. 1A).

Figure 4A:
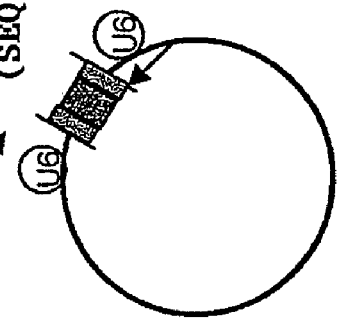

Another embodiment of the inventive method does not require host cells producing recombinase. In accordance with this embodiment of the inventive method, a random or semirandom oligonucleotide sequence flanked by restriction sites is made double stranded after priming with a primer complementary to the 3' restriction site using standard methods known in the art. The oligoDNAs are bounded by restriction sites and followed by a priming sequence. Preferably, the random sequence is between about 15 and about 30 nucleotides, and most preferably is about 20 nucleotides. The priming sequence is preferably at least about 5 nucleotides. This initial population of random or semirandom oligoDNAs is cloned directly into a suitable RNA expression vector between two RNA polymerase promoters (i.e., a first RNA promoter and an second RNA promoter). The two RNA polymerase promoters are oriented "inward" so as to direct RNA transcription in opposite directions, each towards the other RNA promoter on the opposite strand. Preferably, the initial population of oligoDNAs is cloned immediately between the two promoters, or positioned between the two promoters with few (e.g., less than about 10, such as less than about 5) base pairs between the random or semirandom sequences and the flanking first and second RNA promoters. In some instances, when cloned into the plasmid between the two polymerase promoters, the random or semirandom sequence may be immediately flanked by 5'polyA (e.g., AAAAA) and/or by polyT3' (e.g., TTTTT) by engineering the initial oligoDNAs to contain the random or semirandom sequence flanked by the preselected polyA and polyT sequences. These sequences terminate transcription from certain RNA polymerase promoters such as U6 and H1 [see Method 2, FIG. 4A]. Preferably, at least one of the promoters is an H1 or a T7 promoter, or both of the promoters are T7 promoters and are flanked by class II T7 terminators, or more preferably the two promoters differ from each other, e.g., one promoter is a U6 promoter and the other a H1 promoter (see, e.g., FIG. 4B). As described above, the oligoDNAs also can (and preferably do) contain 3' and 5' restriction sites for facilitating cloning.

Finally, the RNA expression vectors are pooled to form a library of similar vectors containing different random or semirandom DNA between the first and second promoters.

It will be appreciated that, in this embodiment, after the population of initial oligoDNAs has been cloned into the RNA expression vector between the two RNA promoters, the first and second RNA promoters direct transcription of the respective sense and antisense strands of the random or semirandom sequence placed between them. Dual transcription of the sense and antisense random or semirandom sequences of a plasmid within a host cell will result in primary complementary transcripts that can self-anneal to form siRNA within host cells. Where no flanking polyA or polyT sequences are included in the initial population of oligoDNAs (or included in the RNA expression vector flanking the site of insertion of the initial oligoDNAs sequences), RNA transcription will continue past the random or semirandom sequences. However, suitable termination sequences are present in the sequence antisense to many RNA promoters. Thus, for example, where the first or second RNA promoter is a U6 promoter, a suitable termination sequence (CATTTTA) is found about 70 base pairs into the opposite promoter. The additional amount of transcribed sequence will be cleaved off by the DICER enzyme within the cell. Thus it is preferred for one or both of the first and second RNA promoters in the expression vector of this embodiment to be a U6 RNA promoter. In another embodiment, a hairpin [sense-antisense] RNA-coding cassette can be placed between the two promoters to increase the expression from that hairpin cassette.

A similar approach can be employed wherein the promoter is a T7 promoter. In this embodiment, the initial oligoDNAs can include the random or semirandom sequence flanked distally by a T7 stop sequence in opposite orientations and proximally by a T7 promoter in opposite orientations (i.e., first and second T7 promoters, oriented inward) [see Method 3, FIG. 5]. The T7 promoter preferably is a truncated 19-base pair promoter sequence (e.g., TAATACGACTCACTATAGG (SEQ ID NO:2)), as this minimizes overlap with the complementary strand. However the full 23 base pair T7 promoter also can be used. The oppositely-oriented promoters flank restriction sites for facilitating cloning into the plasmid. Also, in this embodiment, the T7 stop sequences preferably are class II T7 terminators (see, e.g., Macdonald, J Mol Biol, 232, 1030 (1994), an exemplary sequence being CATCTGTTT (SEQ ID NO:3)). As opposed to classic class I terminators, class II T7 terminators do not form hairpin loops and therefore do not block transcription initiation of the T7 promoter immediately 3' to them.

After cloning into a suitable plasmid (or other vector), transcription from each of the first and second T7 promoters proceeds through the random or semirandom sequence and through the opposite T7promoter before encountering the stop sequence. The resulting transcripts will be roughly 60 base pairs long (depending on the length of the random or semirandom sequence). However, only the complementary (sense and antisense) random or semirandom sequences anneal to form the double stranded DNA construct. As a further variation on this embodiment, the RNA expression vector can additionally contain a cassette encoding a T7-derived RNA polymerase having a nuclear localization signal and a domain rendering it responsive to tamoxifen, as noted above.

In another embodiment, the initial oligoDNA population includes oligoDNAs having the following sequence: (5' to 3') a preselected restriction site, an optional AA dinucleotide sequence, the random or semirandom sequence, a first sequence contributing to a priming loop, a spacer sequence, and a second sequence contributing to a priming loop. The first sequence contributing to a priming loop the second sequence contributing to a priming loop should anneal to form a loop, and preferably these sequences are complementary to each other [see Method 4, FIGS. 6A-6B]. The first and second sequences contributing to a priming loop can include from about 3 to about 10 base pairs each, and need to anneal to each other to form a loop. Preferably, the sequences include between about 4 and about 6 base pairs. In one embodiment, the first sequence contributing to the priming loop is a GC-rich sequence and the second sequence contributing to a priming loop also is a second GC-rich sequence, one preferred CG-rich sequence being CCGG. The spacer sequence preferably includes between about 3 and about 10 base pairs, more preferably between about 4 and about 6 base pairs, so as to facilitate forming a loop between the first and second sequences for forming a priming loop. The spacer also should inhibit the formation of double strands with other oligoDNAs in the population (i.e., through cross-annealing of the GC-rich sequences). One preferred sequence for the spacer is AGAG.

The resulting self-annealing loop is used to prime synthesis of the complementary strand of the synthesized DNA (i.e., antisense of the random or semirandom sequence). This is achieved by exposing the oligoDNAs to a DNA polymerase under suitable conditions to extend the complementary strand from the end of the second GC-rich sequence through the template strand preselected restriction site, resulting in a double stranded DNA oligomer. Suitable methods of complementary strand synthesis are well known in the art (see, e.g. *Molecular Cloning: a laboratory manual*, Sambrook et al., A4.22-A4.23 (2001)). However, to preserve the self-annealed loop structure of the oligoDNAs during RNA polymerization, synthesis of the reverse strand most preferably is conducted at or near room temperature, which avoids denaturization of self-annealed DNA.

Following extension, the DNA oligomers are denatured to form single stranded DNAs. Denaturing of double stranded DNA can be achieved by any suitable method known in the art, such as, for example, a denaturing gel, heat treatment, and alkaline denaturing solutions. The single stranded denatured extended oligoDNAs then are isolated. After isolation, the extended oligoDNAs are primed for complementary strand synthesis using sequences engineered into the 5' end of the initial oligoDNAs [see Method 4, FIGS. 6A-6B].

The complementary strands are synthesized, desirably via in vitro DNA synthetic methods, through the 5' terminus of the template strand. Synthesis of the complementary strands can be achieved by any suitable method known in the art; however it is important to synthesize the complementary strand under conditions that minimize or prevent self-annealing of the complementary portions of the template, which prevents synthesis of the complementary strand. At room temperature, this will result in extremely low yield, if any. Even some successful formation of shRNA-coding sequence would not be random because of preferable self-annealing by GCrich sequences (compared with AT-rich sequences) and dropping out of these sequences from the random pool One way of minimizing self-annealing of the template is to conduct the synthesis of the complementary strand at denaturing temperatures, such as greater than about 50° C. Preferably, the temperature for synthesis is between about 60° C. to about 75° C., and most preferably, the temperature for synthesis is about 65° C. to preserve denaturization of the template during DNA synthesis. Of course, a polymerase suitable for conducting the synthesis at such elevated temperatures (e.g., Taq, Taq Stoffel fragment, rTth, Tfl, Hot Tub, Tbr, UlTma, rBst, Isotherm Bst large fragment, Pwo, Tli, DeepVent, and Pfu, etc.)) should be employed However, it is within the ordinary skill to select a suitable enzyme and reaction conditions to synthesize complementary DNA. As an alternative, or in addition to employing high-temperature conditions to synthesize the complementary strand, complementary strand formation can be conducted in the presence of enzymes that facilitate single strand invasion of the primer onto the template. Nonlimiting examples of such enzymes include enzymes of the *E. coli* recA and recE/rec/T pathways (see, e.g., Gamper et al., *Biochem*, 42(9), 2643-55 (2003) and Noirot et al., *J. Biol. Chem.*, 273(20), 12274-80 (1998)), and similar enzymes of similar pathways in other organisms also can suitably be employed.

Following synthesis, the double stranded siRNA-encoding DNAs comprise two complementary random or semirandom sequences, flanked by the preselected restriction site and separated by a spacer sequence, wherein the first sequence is the antisense sequence of the second sequence. At this stage, the population of siRNA-encoding DNAs can be pooled to form an siRNA-encoding library. Alternatively, the siRNA-encoding DNAs can be digested with the restriction enzyme corresponding to the preselected restriction site cloning into RNA expression vectors, such as those mentioned above. Desirably, the cassette is introduced into such vectors between a suitable RNA polymerase promoter and an operable RNA polymerase termination sequence. After such cloning, the resulting RNA expression vectors can be pooled to form an siRNA library.

In another preferred embodiment, the invention provides a method for producing an siRNA library that does not involve synthesizing of short oligoDNAs containing a random or semirandom sequence. This embodiment is advantageous for analysis of RNA transcribed by a cell rather than relying on randomly generated DNA oligomers. Any suitable cDNA library can be used, many of which are commercially available or can readily be produced by those skilled in the art. If desired, the cDNA library from the organism of interest can optionally be digested with a desired restriction enzyme. The restriction enzyme is selected to produce digest fragments between about 100 and about 1000 base pairs in length. (e.g. HaeIII, Sau3A, MboI, etc). Of course, the entire length of the cDNA can be used, if desired.

Figure 7A:
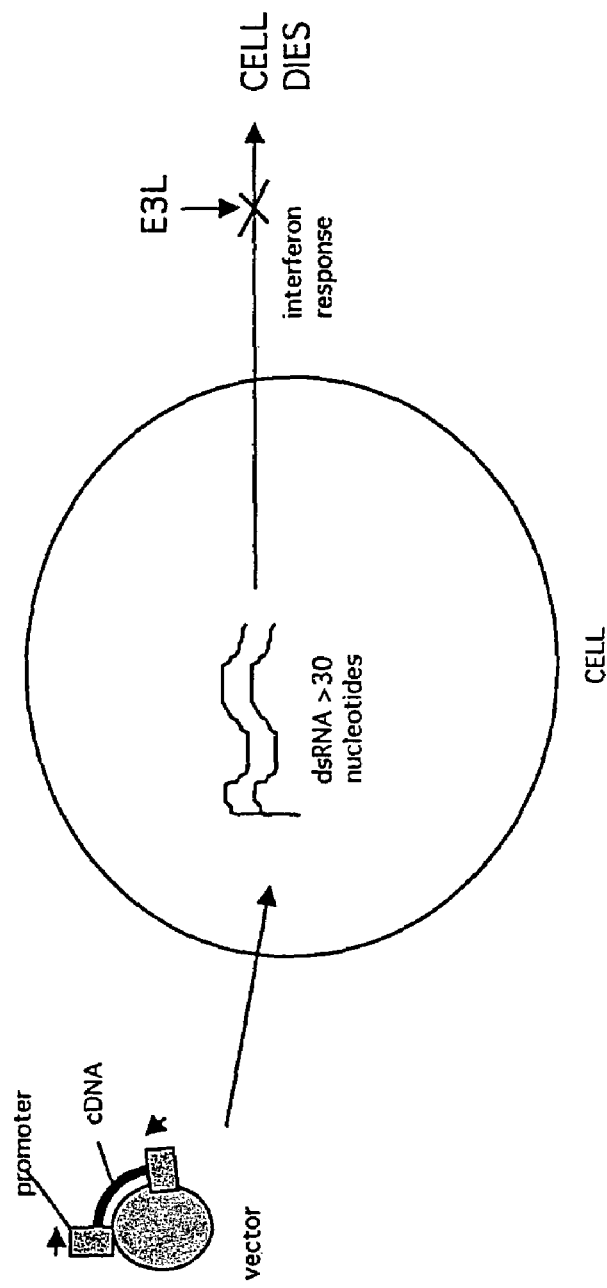

The cDNA (or digest fragments thereof) are cloned into a plasmid using any suitable cloning technique. The plasmid used for cloning should have bi-directional transcription from RNA Polymerase promoters upstream of the sense and antisense strand. The plasmid also can have either the E3L gene or the E3L gene as a fusion gene with a gene for a selectable marker, in cis with respect to the cloning site [see Method 5, FIGS. 7A-7B]. Examples of selectable marker genes include, but are not limited to GFP, Neo, Puro, and others are known to those of ordinary skill in the art. As an alternative to the plasmid having the E3L gene, the E3L gene can be stably or inducibly expressed endogenously or from another exogenous expression cassette within cells used for testing the library. For example, a constitutive or inducible E3Lexpressing plasmid can first be transfected/transduced into the cell (transiently or stably) before the random library. It is desirable for E3L protein activity to be regulable. For example, expression of the E3L gene can be under the control of an inducible promoter. Alternatively, the E3L protein can be regulated on a post-translational basis (e.g., as a fusion protein with a tag, such as a steroid hormone receptor rendering E3L activity inducible by a cognate ligand). The E3L gene inhibits interferon-induced double stranded RNA dependent pathways (see, e.g., Garcia et al., *Oncogene*, 21, 8379 (2002); xiang et al, *J. Virol.*, 76, 5251 (2002)). Because the E3L gene and the double-stranded RNA are transfected into the cells in cis, the interferon-response to longer double stranded RNA is inhibited, and relatively long double stranded RNA transcripts do not lead to cell death as a result. However, the DICER enzyme cleaves the long double stranded RNAs generating siRNAs of about 15-30 base pairs in length, which can anneal to form siRNAs within the host cell. This embodiment has advantages over other approaches in which siRNAs are generated against cDNA libraries either by "brute-force" cloning of siRNAs against hundreds or thousands of targets, or libraries comprised of short pieces of cDNAs (eg under 35 bp) such as those based on Mmel digestion. In this embodiment, large double stranded RNAs are naturally processed by the Dicer enzyme within the cells into siRNAs. This is a more efficient process leading to optimally effective short siRNA fragments (Tijsterman, et al., *Cell;* 117:14 (2004) and references therein). Recipient cell lines intended for phenotypic screening using the siRNA library can alternatively be engineered to stably contain an inducible E3L gene (for example fused with an estrogen receptor domain, conferring tamoxifen dependence). This can be induced by tamoxifen just before transfecting the cells with the library coding for long double stranded RNAs.

It will be understood that, having provided a method for constructing a siRNA library, the invention provides a siRNA library suitable for use in cells derived from higher organisms, particularly mammalian cells. Desirably, the libraries include a population of cassettes encoding random or semirandom siRNAs, which comprise complementary sense and antisense sequences of between about 12 and about 35, such as between about 15 and about 30 nucleotides (desirably between about 19 and about 23 nucleotides).

The invention also provides plasmids for expressing siRNA (or shRNA). A suitable plasmid for expressing random or nonrandom siRNA (or shRNA) contains oppositely oriented U6 and H1 promoters with a cloning site for siRNA-coding sequence between them such that sense and antisense strands of the inserted sequence are transcribed. Preferably, the U6 promoter within such a plasmid contains 27 or 28 bp of U6 coding sequence prior to the cloning site, which may enhance siRNA stability. Another preferred plasmid permits the inducible expression of siRNA by exposure to a recombinase (such as FLP). Such a such plasmid contains a polymerase III promoter followed by a recombinase site (eg FRT), a spacer sequence containing within it a polythymidine repeat (four or more T's in a row), followed by a second site for the recombinase in the same orientation as the first, and finally a cloning site for a shRNA coding-hairpin. Preferably, the siRNA-coding sequence within such a plasmid is flanked by opposing polymerase III promoters, in which one of the promoters has inserted a recombinase site-polythymidine-recombinase site cassette 5' to the siRNA-coding sequence. Using such a plasmid, the invention provides a method of regulating the expression of siRNA using recombinases of the integrase family (e.g., FLP). Upon exposure to the recombinase, recombination events within the plasmid will remove the polythymidine repeat, which acts as a termination sequence. The removal of the polythymidine repeat, thus, will permit the polymerase to express the coding si-coding sequence. In such a method, the recombinase protein preferably is inducibly expressed, for example, by a regulable promoter, or as a fusion with estrogen-receptor, so that the recombination events, and expression of the siRNA (or shRNA) can be controlled.

In another aspect, the invention provides a method of using a siRNA library. For example, a siRNA library can be used to identify genes or non-coding sequences corresponding to a resulting behavioral, biochemical, chemical, functional, molecular, morphological, phenotypic, or physical property. Genes or non-coding sequences corresponding to resulting behavioral, biochemical, chemical, functional, molecular, morphological, phenotypic, or physical properties can include, but are not limited to, genes or non-coding sequences involved in tumor suppression, oncogenesis, apoptosis, metastasis, signal transduction (e.g., in normal and diseased cells), viral proteins or synthesis, pathogenic pathways, identification of known or unknown bioweapon susceptibilities, identification of genetic sequence and susceptibilities of agents causing emerging infections, and lytic pathway requirements, as well as other genetically related behavioral, biochemical, chemical, functional, molecular, morphological, phenotypic, or physical properties known in the art. An siRNA library also can be used to generate a subpopulation of cells that exhibit common behavioral, biochemical, chemical, functional, molecular, morphological, phenotypic, or physical properties as a result of being exposed to the library. Such a subpopulation of cells can be used, for example to screen candidate drugs or other agents impacting the desired behavioral, biochemical, chemical, functional, molecular, morphological, phenotypic, or physical properties.

Figure 8:
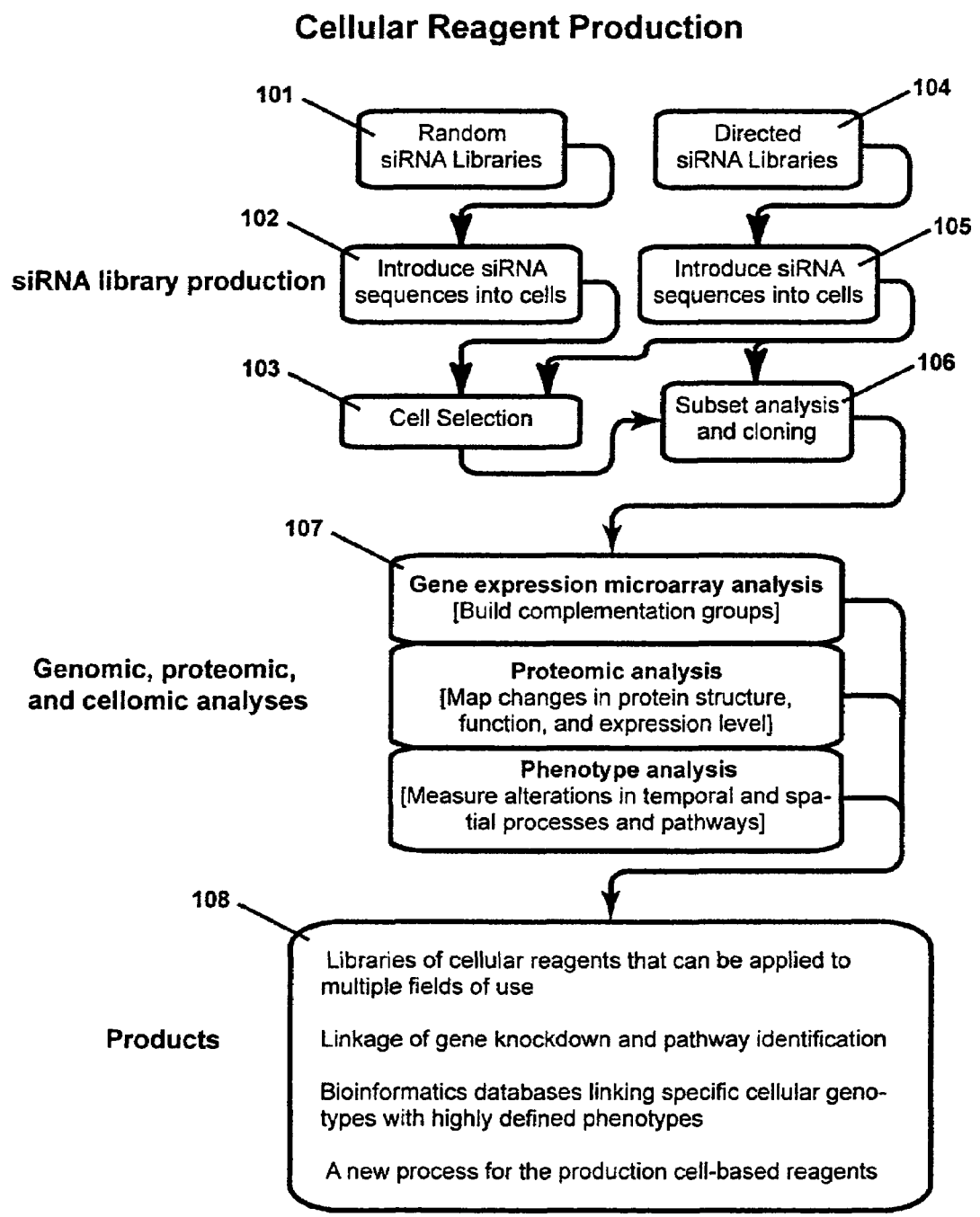
FIG. 8 is a flowchart illustrating the use of a random siRNA library.

A flowchart demonstrating this method is presented as FIG. 8. As noted above, a random (or semirandom) siRNA library 101 or a directed siRNA library (directed only against cDNA, or even against a subset of cDNAs) 104 first is produced. The siRNA library then is introduced into a population of cells 102, 105. The population of cells then is subjected to a selection process 103 to select a subpopulation of cells exhibiting a different behavioral, biochemical, chemical, functional, molecular, morphological, phenotypic, or physical property from the remainder of population. Following the selection process 103, the subpopulation (i.e., subset) of cells can be isolated, analyzed, and/or cloned 106 as desired. Such analysis of the subpopulation can be identification of the siRNA species responsible for the different properties of the subpopulation relative to the remainder of the population. Alternatively, the subpopulation can be further analyzed by genomic, proteomic, and/or cellomic assays 107. Where such genomic, proteomic, and/or cellomic assays are employed, the method can produce several useful bioinformatics products 108.

The inventive method pertains to the use of any siRNA library, which can be or comprise a random or semirandom siRNA library 101, as described herein, or a directed siRNA library (e.g., directed only against cDNA, or even against a subset of cDNAs) 104. The libraries 101, 104 can be constructed as described herein. In accordance with the inventive method, after constructing the library 101, 104, the siRNA library sequences 101, 104 are introduced into a population of cells 102, 105. Any suitable method can be employed to introduce the siRNA libraries 101, 104 into the cells 102, 105. For example, an siRNA library 101, 104 comprising siRNA molecules can be introduced into the population of cells 102, 105 directly. Alternatively, where the library 101, 104 comprises a population of vectors having transcription cassettes encoding siRNA, the library 101, 104 can be introduced into the population of cells 102, 105 by transfecting the cells with the vectors, if they are plasmid vectors, or by infecting the cells with viral vectors comprising the library. Where the library 101, 104 is delivered into the population 102, 105 by transfecting or infecting the population with a vector system encoding the siRNA library, preferably, the population of cells is transfected/infected with the library in about a 1:1 ratio such that each cell within the population only transcribes a single siRNA species from the library. However, transfection of multiple siRNAs into each cell can substantially increase the efficiency of screening at the cost of additional analytical steps. Multiple specific siRNAs have been shown to be functional within a single cell (Yu, Molecular Therapy, vol7, 228-236 (2003)).

The population of cells can include any desired cell type, and desirably are cells derived from higher organisms (e.g., eukaryotes, preferably mammals, such as humans). It is within the ordinary skill of the art to select a suitable population of cells, and the artisan will be guided in this selection by the desired behavioral, biochemical, chemical, functional, molecular, morphological, phenotypic, or physical properties that are being investigated through use of the library. However, where the library 101, 104 is to be introduced into the population of cells 102, 105 as a vector system (e.g., a plasmid or viral vector system containing expression cassettes encoding the library), the population of cells 102, 105 should be compatible with the vector system such that the siRNA-encoding sequences within the vectors will produce the siRNA within the population of cells.

Following introduction of the library 101, 104 into the population of cells 102, 105, the population is subjected to a selection process 103 to select cells (or subpopulations or clones of cells) that can be distinguished from the remainder of the population on the basis of a behavioral, biochemical, chemical, functional, molecular, morphological, phenotypic, or physical change or property. Examples of behavioral, biochemical, chemical, functional, molecular, morphological, phenotypic, or physical changes resulting from specific stimuli include, but are not limited to, cell death, uncontrolled or abnormal cell growth, changes in color, altered protein synthesis, altered cell morphology, altered cell differentiation, and altered cellular metabolism, altered cell motility as well as other related phenotypes.

In accordance with the selection process 103, following introduction of the library 101, 104 into the population of cells 102, 105, the cells are observed to detect behavioral, biochemical, chemical, functional, molecular, morphological, phenotypic, or physical changes or properties of the cells. In some embodiments, the population is subjected to a stimulus that can precipitate a behavioral, biochemical, chemical, functional, molecular, morphological, phenotypic, or physical change within some cells within the population. Such stimuli can include, but are not limited to, exposure to alterations in physical conditions, (such as temperature changes, placement in a particular type of culture device or substrate, exposure to light or darkness, exposure to irradiation, etc.), exposure to one or more agents affecting cell growth, exposure to one or more agents affecting cellular metabolism, exposure to one or more agents affecting cellular movement, exposure to one or more agents affecting cellular stress responses, exposure to one or more chemicals, such as toxins, exposure to one or more differentiating agents, exposure to one or more trophic factors, exposure to one or more viruses (which can be a known virus, or an unknown virus), as well as other stimuli known in the art to result in a particular phenotype. The stimulus can be selected to have a known, expected, or predictable effect on the population of cells (but for the effect of siRNA within the library) or the stimulus can be selected without knowledge of its effect on the population of cells.

Differential behavioral, biochemical, chemical, functional, molecular, morphological, phenotypic, or physical change or response of certain cells within the population relative to the remainder of the population permit such cells to be selected 103 as a subset or "subpopulation" 106 in accordance with the inventive method. For example, a subpopulation 106 of cells can be selected 103 as including those cells not exhibiting an expected behavioral, biochemical, chemical, functional, molecular, morphological, phenotypic, or physical property or change in response to a stimulus, if the stimulus was selected to precipitate a known or predictable change. Alternatively, a subpopulation 106 of cells can be selected 103 as those cells exhibiting a behavioral, biochemical, chemical, functional, molecular, morphological, phenotypic, or physical response to the stimulus that the remainder of the population does not exhibit.

It will be observed that the subpopulation 106 can be selected 103 on the basis of any measurable behavioral, biochemical, chemical, functional, molecular, morphological, phenotypic, or physical property or change. The assessment of such properties and/or changes varies depending on the property that is being assessed, but assaying for such changes is within the ordinary skill of the art. For example, where a change is morphological, a subpopulation 106 of cells can be manually selected 103 based on observed morphological features. Similarly, where a change or property is biochemical, the subpopulation 106 of cells can be selected 103 based on the appropriate biochemical assay (e.g., a change in color may facilitate selection 103 of a subpopulation 106).

A non-limiting example involves selecting 103 a subpopulation 106 based on the effect of the siRNA library on cell motility or invasiveness. Such properties can be assayed by introducing the population of cells into a device that restricts the movement of cells from one part of the device to the other, such as a Boyden chamber. In such a device, the cells can be permitted to migrate across a restrictive barrier. After migration has been allowed to occur, cells that have enhance invasiveness activity are retrieved from the side of the barrier opposite to the site of application and cells that have inhibited invasiveness activity are retrieved from the original site of application. The two subpopulations of cells then can be isolated and further studied, as described herein, to assess the effect of siRNA on cell motility and invasiveness.

As another non-limiting example, after introduction of the siRNA library into the population, a subpopulation 106 can be selected 103 for changes in their cell-sensitivity to agents that are cytotoxic or that induce apoptosis. To select 103 such a subpopulation 106, the siRNA-library-modified cell population can be cultured under conditions that expose the population to one or more stress agents (such as chemical or biological compounds or toxins, light energy of multiple wavelengths, ionizing radiation, heat, cold, electricity, sound waves, or a combination thereof). An especially effective selection technique is to expose the population of cells (after introducing the library into the population) to etoposide at concentrations that range from 1 nM to 1 mM for periods of time that range from 1 min to several hours to several days. A subpopulation 106 can thus be selected 103 to include those cells that survive this treatment.

As another non-limiting example, the effect of the siRNA library on cell growth can be assessed by exposing the population to one or more agents that selectively kill cells that continue to grow. These agents include, but are not limited to, nucleic acid analogs such as 5-flurorouracil or microtubule modulating drugs such as paclitaxel. A subpopulation 106 can thus be selected 103 to include those cells that survive this treatment. As another non-limiting example, an assay can be designed to link an easily-recognized property (e.g., survival in a given medium) to the desired change. For example, to assay for differentiation (a potentially difficult-to-assay phenotypic change) less-differentiated cells deficient in thymadine kinase (TK) (such as mouse embryonic stem cells—see e.g., Dobrovolsky, *Mol. Genet Metab.*, 78(1):1-10 (2003)) can be engineered to contain an exogenous TK expression cassette placing TK under the control of a promoter controlled by a gene product differentially expressed during development. For example, as embryonic stem cells differentiate, the activity of the Rex-1 promoter in such cells is attenuated. Thus, where the TK cassette is placed under control of the Rex-1 promoter in mouse embryonic stem cells that lack endogenous TK, cells that differentiate, for example in response to exposure to an agent, will cease to express TK in appreciable amounts. Such a subpopulation 106 can be selected 103 by culturing the cells in a medium (e.g., HAT medium) that kills cells expressing TK (which, in this exemplary assay system, will be undifferentiated embryonic stem cells). In this system, a subpopulation 106 can be selected 103 as the cells that survive in the HAT medium. Similar selection could employ TK-expression linked to other genes whose expression is a marker of the undifferentiated state in the case of embryonic stem cells (Niwa, Nat Genet. 2000 April; 24(4): 372-6.) For example TK driven by the Oct 3/4 promoter could be used to dissect pathways involved in the transition to trophectoderm.

By whatever method it is selected, the subpopulation (or subset) 106 selected in accordance with the inventive method contains cells having siRNA that are candidates for having a causal relationship to the behavioral, biochemical, chemical, functional, molecular, morphological, phenotypic, or physical differences between the cells within the subpopulation relative to the population of cells at large. In some embodiments, the subpopulation can be physically isolated from the general population of cells 106. Accordingly, the invention provides such a subpopulation of cells substantially isolated from the initial population of cells. Preferably, the subpopulation is completely isolated from the initial population of cells. Moreover, it may be desirable to clone or culture the subpopulation as well 106. Accordingly, the invention provides the subpopulation of cells as a clonal population. The subpopulation can be isolated and/or clonally expanded 106 by methods known to those of ordinary skill in the art.

After selecting the subpopulation, the inventive method further involves analysis of the subpopulation 106. The subpopulation can be analyzed 106 in any suitable manner depending on the nature of the information sought. For example, the subpopulation can be analyzed 106 behaviorally, biochemically, chemically, functionally, molecularly, morphologically, phenotypically, or physically. The nature of the analysis can be, for example, an assessment of the differences between the subpopulation and the initial population, or, if desired, an assessment of the features common the cells within the subpopulation.

As noted, the siRNAs from cells within the subpopulation (which exhibit a behavioral, biochemical, chemical, functional, molecular, morphological, phenotypic, or physical property different from the main population) are considered candidates for inhibiting genes or noncoding regions that modulate the behavioral, biochemical, chemical, functional, molecular, morphological, phenotypic, or physical property of interest. Accordingly, in one embodiment of the inventive method, the subpopulation can be analyzed 106 by isolating siRNA (e.g., the siRNA expression cassettes) from the cells of the subpopulation for further study, which can include reiterative assays or sequencing the isolated siRNA. Methods of isolating candidate siRNAs include, for example, reverse transcription—polymerase chain reaction (RT-PCR), which is a technique well known in the art. Alternatively, if the siRNA library is employed as a retroviral expression vector, then siRNA candidates can be rescued by transfecting cells within the subpopulation with a retroviral helper plasmid so as to package the retroviral vector containing the candidate siRNA into a non-replicative retrovirus, which can be isolated from the supernatant of the cells. Such a retrovirus containing candidate siRNA can then be employed in a second or subsequent round of assay to identify functional genes in a retroviral cDNA library (see, e.g., Bhattacharya et al., *Proc. Nat. Acad. Sci.* (*USA*), 99, 8838 (2002). Accordingly, the invention includes the siRNA isolated from the subpopulation of cells, as described herein. Such siRNA can comprise a collection of disparate sequences or be substantially or completely homogenous.

Thus, the method can involve introducing the library into a population of cells, exposing the population of cells to a stimulus that causes a known phenotypic change, identifying cells within the population that do not exhibit the phenotypic change, and rescuing the siRNA from the cells. The siRNA from the cells then can be sequenced and compared against a database, or used to generate a probe for identifying a genetic sequence that is a candidate for involvement in the particular phenotypic change of interest. The siRNA library described by this invention will be useful in rapid functional identification of critical genes involved in cancer, cell differentiation, viral infection, bacterial pathogenesis, metabolic pathways, signal transduction pathways, lytic pathways, as well as other research fields relying on phenotypic analysis. Specific siRNAs identified through this process may have direct therapeutic value.

Also as noted, the cells within the subpopulation (which exhibit a behavioral, biochemical, chemical, functional, molecular, morphological, phenotypic, or physical property different from the main population) are considered candidates for harboring siRNAs that inhibit genes or noncoding regions that modulate the behavioral, biochemical, chemical, functional, molecular, morphological, phenotypic, or physical property of interest. Accordingly, in another embodiment of the inventive method, the subpopulation can be further analyzed by genomic, proteomic, cellomic methods, or combinations thereof 107. As an example of genomic analysis, the gene expression of the cells within the subpopulation can be assessed, e.g., by microarray analysis. This can facilitate the construction of complementation groups of genes, for example. That is, the effect of siRNAs generated from the random library leading to a common cell selection phenotype could affect distinct or overlapping genetic pathways. Proteomic analysis can involve mapping the changes in protein structure, function, activity, and/or expression level within the subpopulation. Proteomics assessment can focus on single, multiple, or proteome-wide proteins found within the cells of the subpopulation. Cellomic analysis can, for example, involve an assessment of cellular properties and pathways (such as behavioral, biochemical, chemical, functional, molecular, morphological, phenotypic, or physical). Such properties can be assessed temporally and spatially to develop profiles of the types of cells within the subpopulation or of the subpopulation as a whole. These parameters include, but are not limited to, "high-content measurements" such as measurements of signal transduction events, cell cycle regulatory events, metabolic activity, changes in cell shape and motility, translocation of molecules between intracellular organelles and compartments, and molecular events associated with cell death or apoptosis.

Of course, genomic, proteomic, and cellomic analysis of the subpopulation are not mutually exclusive; such modes of analysis can be employed separately or in combination. The databases generated from all cellular measurements form the basis for a knowledge base that links the information gained from genomic, proteomic, and cellomic analyses. Such information can yield several products 108 useful in bioinformatics. For example, the method can produce libraries or batteries of cells (isolated from the subpopulations) that have common behavioral, biochemical, chemical, functional, molecular, morphological, phenotypic, or physical characteristics. Such libraries or batteries can serve as reagents for multiple uses, such as screening candidate drugs, identifying unknown toxins or infectious agents, etc. The combined use of genomic, proteomic, and cellomic analysis also can produce a knowledge-base of information linking particular gene attenuation with biological pathways. The combined use of genomic, proteomic, and cellomic analysis also can produce a knowledge-base of information linking particular gene attenuation with cellular phenotype. Such knowledge can help identify targets for putative therapeutic intervention, for example. The method also can produce bioinformatics databases linking specific genotypes with highly defined phenotypes. The combined use of genomic, proteomic, and cellomic analysis also can lead to a new process for the production of cell-based reagents.

As a non-limiting example, it is noted above that the selection process 103 can involve selecting a subpopulation of cells exhibiting differential motility or invasiveness activity. Further analysis of the subpopulations can involve isolating, cloning and expanding such subpopulations 106 such that cell lines are produced that either constitutively express a particular phenotype or express a phenotype in an inducible form (e.g. if an inducible random siRNA library 101 was introduced into the cells 102). The phenotype is then dissected molecularly using genomic, proteomic, and cellomic analyses 107. Thus, for example, gene expression patterns can reveal changes in mRNA levels coding for single, multiple, or genome-wide sequences that are associated with altered invasiveness activity. Alternatively or in complementation to the gene expression patterns, changes in the structure, activity, and expression level of single, multiple, or proteome-wide proteins found within the subpopulation of cells expressing altered invasiveness activity can be measured. These proteomic measurements can include, but are not limited to, changes in the levels or activity of cytoskeletal proteins responsible for cell motility such as keratins, tubulin, and actin as well as the numerous proteins that are associated with and regulate the cellular cytoskeleton. In further complementation to the genomic and proteomic measurements, temporal and spatial measurements of the molecular processes responsible for the altered cellular invasiveness activity are assessed within subpopulations of single cells.

As another non-limiting example of the combined genomic, proteomic, and cellomic analysis of a subpopulation of cells, it is noted above that the selection process 103 can involve selecting a subpopulation of cells exhibiting altered cytotoxicity and apoptosis properties. Further analysis of the subpopulations can involve isolating, cloning and expanding such subpopulations 106 such that cell lines are produced that either constitutively express a particular phenotype or express a phenotype in an inducible form. The phenotype is then dissected molecularly using genomic, proteomic, and cellomic analyses 107. Genomics assessment of such a subpopulation can identify gene expression patterns that reveal changes in mRNA levels coding for single, multiple, or genome-wide sequences associated with altered cytotoxicity or apoptosis activity. Proteomics assessment can involve measuring changes in the structure, activity, and expression level of single, multiple, or proteome-wide proteins found within the cells expressing altered cytotoxicity or apoptosis. These measurements can include, but are not limited to, changes in the levels, intracellular localization, or activity of proteins responsible for apoptotic cell death such as the caspases, cytochrome c, or PARP. Cellomics assessment can involve temporal and spatial measurements of the molecular processes responsible for the altered cellular toxicity or apoptosis activity within populations of single cells. The product from the combined use of genomic, proteomic, and cellomic analysis of such a subpopulation will be libraries of cells that contain identified siRNA's that inhibit/knockdown identified non-coding regions of DNA that might be regulatory regions and/or coding regions that knockdown either known or unknown genes/proteins. The genomic, proteomic and cellomic data on each cell type can be used to construct a database of library characteristics. These characterized cell lines can be used in screening for cytotoxicity/apoptosis of known and unknown compounds.

As another non-limiting example of the combined genomic, proteomic, and cellomic analysis of a subpopulation of cells, it is noted above that the selection process 103 can involve selecting a subpopulation of cells exhibiting altered TK-promoter expression, and preferably altered differentiation activity. Further analysis of the subpopulation can involve isolating, cloning and expanding such subpopulation 106 such that cell lines are produced that either constitutively express a particular phenotype or express a phenotype in an inducible form. The phenotype is then dissected molecularly using genomic, proteomic, and cellomic analyses 107. Genomics assessment of such a subpopulation can identify gene expression patterns that reveal changes in mRNA levels coding for single, multiple, or genome-wide sequences that are associated with the altered differentiation phenotype. Proteomics assessment of such a subpopulation can involve measuring changes in the structure, activity, and expression level of single, multiple, or proteome-wide proteins found within the cells associated with differentiation. These measurements can include, but are not limited to, changes in the levels, intracellular localization, or activity of proteins responsible for cell signaling (e.g., hormone secretions and the expression of receptors), regulation of genetic expression (such as transcription factors), and differentiation markers. Cellomics assessment can involve temporal and spatial measurements of the molecular processes responsible for the altered differentiation behavior within populations of single cells. The product from the combined use of genomic, proteomic, and cellomic analysis of such as subpopulation will be libraries of cells that contain identified siRNA's that inhibit/knockdown identified non-coding regions of DNA that might be regulatory regions and/or coding regions that knockdown either known or unknown genes/proteins. The genomic, proteomic and cellomic data on each cell type can be used to construct a database of library characteristics. These characterized cell lines can be used in screening for the effect on cellular differentiation of known and unknown compounds.

The following examples further illustrate the invention but, of course, should not be construed as in any way limiting its scope.

EXAMPLE 1

This example demonstrates a method of preparing a siRNA library [see Method 1A, FIGS. 1A-1C]. Random 20-mers of DNA are generated using a DNA synthesis machine. The 20-mers are flanked by two distinct restriction sites, which are BglII (5') and PstI (3') respectively. The 20-mers and flanking restriction sites are primed using a sequence complementary to the PstI site and 3' flanking sequence. The primed sequences are used to synthesize and extend the complementary strand to each 20-mer and its restriction sites.

Figure 10A:
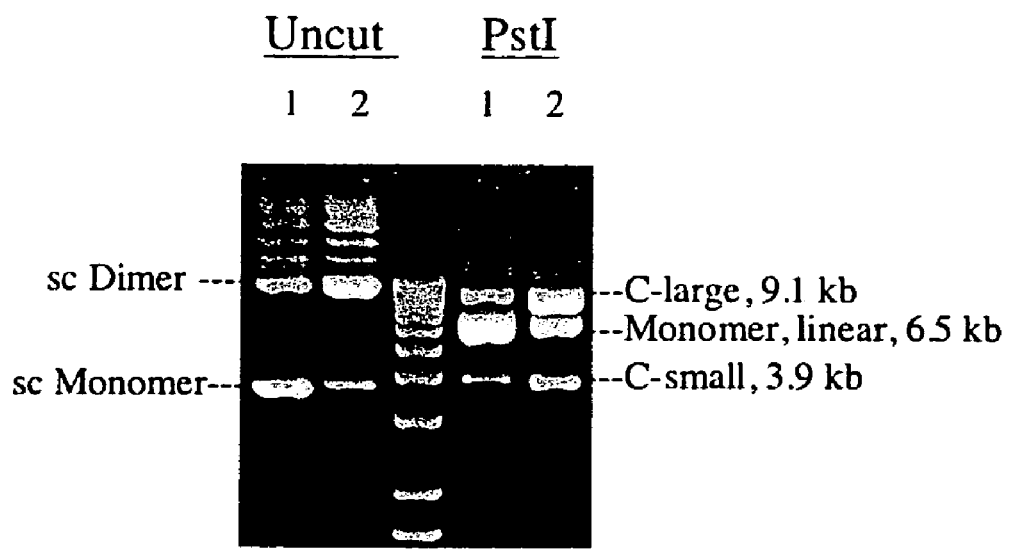
FIGS. 10A and 10B depict gels demonstrating steps in the construction of a random siRNA library using the FLP-FRT system in accordance with method 1 as described below.
Figure 10B:
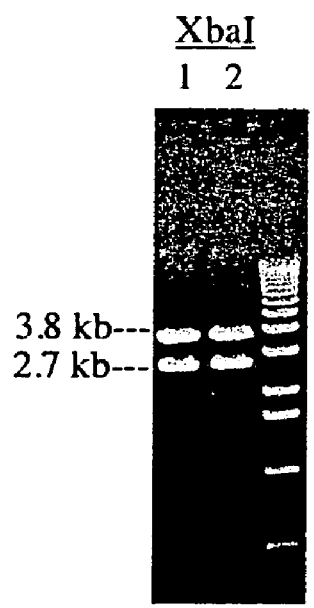

The resulting double stranded DNA 20-mers were cloned into plasmids having FRT sites oriented toward each other and the restriction enzyme sites, BglII and PstI, as well as the coding sequence for FLP recombinase (Sadowski, P D. 1995, Prog Nucleic Acid Res Mol Biol 51:53-91) between the FRT sites [see Method 1A, FIG. 1A]. This plasmid is pFRT. After the 20-mers were cloned into the plasmids, the plasmids were transformed into bacteria. Following bacterial transformation, the FLP enzyme was expressed in the bacteria. Though the action of the FLP-FRT system, an equivalent mix of single plasmids results, containing original (A) or inverted (B) sequence between the recombination sites. As well, FLP generates combined double plasmids (C forms) comprised of both A and B forms. The combined plasmids had two DNA inserts wherein the first DNA insert has a sequence that is the antisense sequence of the second DNA insert. All recombinant plasmids were isolated from the bacteria. Two isolates of plasmid pFRT were investigated, each grown with different amounts of induced FLP activity. Isolate 1 demonstrated more supercoiled (sc) monomer form than isolate 2, and likewise isolate 2 showed more dimer and higher multimer forms than isolate 1 (FIG. 10A). The higher order forms are generated when monomers insert into each other via FLP activity at the FRT sites. However, when isolates 1 and 2 were digester with an enzyme outside of the reversible sequence between the FRTs of pFRT, all of the supercoiled multimer forms digested to two bands at 3.8 kb and 2.7 kb, as expected for the 6.5 kb plasmid (FIG. 10B).

When each of the isolates is digested by the enzyme PstI, several products were formed. The monomer band includes linear A and B form plasmids (see FIG. 1A-1C). In addition the C plasmid, resulting from an A and B combination dimer, resulted in a large and small piece when cut by PstI, asymmetrically placed between the FRTs of pFRT. Isolate 2 had a higher percentage of dimers and therefore results in a higher proportion of C-large and C-small than isolate 1 (FIG. 10A).

The small PstI fragment "C-Small" was isolated and then ligated together. The resulting plasmid was digested with the second enzyme (BglII) to generate small (~50 bp) BglII fragments among other DNA fragments. These small BglII bounded DNA fragments, comprising a cassette containing inverted repeats of 20 nucleotide sequence, were then subcloned into a BamH1 site in retroviral vectors just downstream from a U6 promoter and upstream from a poly T termination site. The resulting vectors include expression cassettes having a U6 promoter upstream of a 20-mer sequence, the antisense sequence to the 20-mer sequence, and an 6 base pair sequence separating the two 20-mer sequences. Finally, the expression vectors were combined to yield an siRNA library (i.e., a library encoding siRNA).

Samples of the resulting libraries were isolated and the sequences of inserts determined. A small sample of clones within the library revealed that the inserts had distinct sequences. Examples of the sequences within this library are as follows (5' to 3'):

```
AGGCGTAACCCCATTAGTTTCTGCAGAAACTAATGG (SEQ ID NO:4)
GGTTACGCCT

TCAGGGTTTTACGTATTGTGCTGCAGCACAATACGT (SEQ ID NO:5)
AAAACCCTGA

TGACCGGCAGCAATAGGAGG CTGCAGCCTCCTATT (SEQ ID NO:6)
GCTGCCGGTCA

TGTTTGGGGGGTGGCTACG CTGCAGCGTAGCCAC (SEQ ID NO:7)
CCCCCCAAACA

AAGTGCGACTAAGGCCGTAA CTGCAGTTACGGCCT (SEQ ID NO:8)
TAGTCGCACTT

AGCTAGGTGGGGTCGCTGG CTGCAGCCAGCGACC (SEQ ID NO:9)
CCCACCTAGCT

GAGGGGAGGCCCTCGCTGGG CTGCAGCCCAGCGAG (SEQ ID NO:10)
GGCCTCCCCTC

AACAGTCGGTGCTCAGGCGG CTGCAGCCGCCTGAG (SEQ ID NO:11)
CACCGACTGTT

GGATAGAGGGAGGTCGCGAA CTGCAGTTCGCGACC (SEQ ID NO:12)
TCCCTCTATCC
```

EXAMPLE 2

This example demonstrates a method of preparing an inducible siRNA library. OligoDNA including random 19-mer sequences flanked by restriction sites (BglII (5') and PstI (3') respectively) are generated using a DNA synthesis machine. The oligoDNAs are primed using a sequence complementary to the PstI sequence. The primed sequences are used to synthesize and extend the complementary strand to each 19-mer and its restriction sites.

The resulting double stranded DNA 19-mers are cloned into plasmids having FRT sites oriented toward each other and the restriction enzyme sites, Asc1 and Fse1, between the FRT sites and containing FLP enzyme coding sequence between the sites. Once the 19-mers are cloned into the plasmids, the plasmids are transformed into bacteria having an inducible FLP recombinase. Following bacterial transformation, the bacteria are express the FLP enzyme. Through the action of the FLP-FRT system, combined plasmids are created. The combined plasmids have two DNA inserts wherein the first DNA insert has a sequence that is the antisense sequence of the second DNA insert.

All recombinant plasmids are isolated from the bacteria. The plasmids are then digested with PstI, gel purified (C-Short) and religated together. This pool of plasmids can then be digested with the second enzyme, BglII. This results in small BglII fragments (~50 bp) among other DNAs. The DNA fragments then are subcloned into an BamH1 site within modified pMIG retroviral vectors immediately downstream from a T7 bacteriophage promoter and upstream from a terminator of T7 transcription (CATCTGTTTT (SEQ ID NO:1)). Upstream from the cloning site, the pMIG retroviral vectors also have a MSCV LTR followed by a coding sequence for T7 polymerase modified to contain an N-terminal SV40 nuclear localization signal and expressed as a fusion protein of an estrogen receptor mutant (G521R), which responds to tamoxifen and not estrogen, as well as an internal ribosomal entry site and GFP (green fluorescent protein) (Welsh and Kay, 1997, Curr Opin Biotechnol 8:617-22) [Method 1C, FIG. 3]. The pooled population of such vectors, each containing the random 19-mer sense and antisense coding cassette, is an inducible siRNA library.

EXAMPLE 3

This example demonstrates an alternate method of preparing an inducible siRNA library. OligoDNA including random sequences (e.g., 19-mers) flanked by restriction sites (BglII (5') and PstI (3') respectively) are generated using a DNA synthesis machine. The oligoDNAs are primed and used to synthesize and extend the complementary strand to each random sequence and its restriction sites.

The resulting double stranded oligoDNAs are cloned into plasmids having FRT sites oriented toward each other and the restriction enzyme sites, BglII and PstI, between the FRT sites. Once the random sequences are cloned into the plasmids, the plasmids are transformed into bacteria having an inducible FLP recombinase. Following bacterial transformation, the bacteria are induced to express the FLP enzyme. Though the action of the FLP-FRT system, combined plasmids are created. The combined plasmids have two DNA inserts wherein the first DNA insert has a sequence that is the antisense sequence of the second DNA insert. All recombinant plasmids are isolated from the bacteria. The plasmids are then digested with PstI and subjected to gel electrophoresis.

DNA fragments containing two DNA inserts are identified via gel electrophoresis (C-short) and excised from the gel. The fragments are autoligated, digested with BglII to liberate the hairpin DNA cassette, which is then cloned into retroviral vectors immediately downstream of a regulatory domain. The domain consists of a poly T termination sequence bound by two FRT sites oriented in the same direction, wherein both FRT sites are either directed toward the 5' terminus or the 3' terminus, and the FRT sites and poly T termination sequence intervene between the U6 promoter and the DNA hairpin cassette cloned downstream of it.

The retroviral vectors can have in cis, an inducible FLP expressed as a fusion protein with a portion of an estrogen receptor mutant (G521R), which responds to tamoxifen and not estrogen, as well as an internal ribosomal entry site and GFP. Induction with tamoxifen releases FLP fusion protein activity to resolve the two FRT sites into one FRT site and eliminating the intervening poly T termination sequence, resulting in expression of the siRNAs. The pooled population of such vectors, each containing the random 19-mer sense and antisense coding cassette, is an siRNA library.

EXAMPLE 4

This example demonstrates an alternate method to prepare a siRNA library. OligoDNAs are synthesized with the following sequence (5' to 3'): an XhoI restriction site, an AA dinucleotide sequence, a random 19-mer sequence, a first GC-rich sequence (GGCC) spacer sequence (GAGA) and, a second GC-rich sequence GGCC) [Method 4, FIGS. 6A-6B].

The first and second CG-rich sequence self-anneal to form a loop, which is used to prime reverse strand synthesis. Reverse strand synthesis is performed at room temperature and the synthesis proceeds through the 5' restriction site on the template strand. The resulting double stranded 19-mers are separated on a denaturing gel, resulting in 38 nucleotide single stranded DNAs, wherein the original 19-mer has a sequence that is antisense to the 19 nucleotide sequence following the second GC-rich region of the DNA.

The single stranded DNAs are primed with the complement sequence 5'-GTCGCTCGAGAA (SEQ ID NO:13) and reverse strand synthesis is carried out with Taq polymerase at a temperature of about 65° C. The resulting double stranded DNAs have a sense 19-mer and an antisense 19-mer on the same strand, in the same transcriptional direction. The double stranded DNAs are digested with Xho1 and cloned into an expression vector. The pooled population of such vectors, each containing a random sense and antisense 19-mer random sequence, is an siRNA expression library.

EXAMPLE 5

This example demonstrates an alternate method to prepare a siRNA library. OligoDNAs, each containing a random 19-mer sequence and having a polyT termination site, flanked by SalI (5') and ClaI (3') respectively, are generated using a DNA synthesis machine. The oligoDNAs are primed using a sequence hybridizing to the 3' end of the oligoDNA, and their complementary strands are synthesized. The resulting double stranded DNA 19-mers are cloned into pMIG retroviral vectors having two U6 promoters (sense and antisense) facing inwards, so as to be between the two U6 promoters and operably linked to each of them such that one U6 promoter transcribes the sense strand of 19-mers and the other U6 promoter transcribes the antisense strand of the 19-mers [Method 2, FIG. 4A]. The pooled population of such vectors, each containing a random 19-mer, is a siRNA library.

EXAMPLE 6

This example demonstrates an alternate method to prepare a siRNA library. OligoDNAs, each containing a random 19-mer sequence and having a polyT termination site, flanked by SalI (5') and ClaI (3') respectively, are generated using a DNA synthesis machine. The oligoDNAs are primed using a sequence hybridizing to the 3' end of the oligoDNA, and their complementary strands are synthesized. The resulting double stranded DNA 19-mers are cloned into pMIG retroviral vectors having one U6 promoters and one H1 promoter facing towards each other, so as to be between the two promoters and operably linked to each of them such that the H1 promoter transcribes the sense strand of 19-mers and the U6 promoter transcribes the antisense strand of the 19-mers [Method 2, FIG. 4B]. The pooled population of such vectors, each containing a random 19-mer, is a siRNA library.

EXAMPLE 7

This example demonstrates an alternate method of preparing a siRNA library. OligoDNAs are generated using a DNA synthesis machine to have the following sequence: a random 19-mer sequence flanked proximally by 19 base pair—T7 promoters oriented to towards each other (i.e., to direct transcription of the random 19-mer sequence) and distally by class II T7 polymerase stop sequences oriented in opposite directions from each other [Method 3, FIG. 5]. The stop sequences at the 5' end of the 19-mers are oriented in the 3' to 5' position, and the stop sequences at the 3' end of the 19-mers are oriented in the 5' to 3' position. Distinct restriction sites further flank the stop sequences such that the restriction sites at the 5' end of the 19-mers differ from the restriction sites at the 3' end of the 19-mers.

The 19-mers with flanking restriction sites are primed using a sequence complementary to the 3' restriction site. The primed sequences are used to synthesize and extend the complementary strand to each 19-mer and its restriction sites.

The resulting double stranded DNA 19-mers are digested at the flanking restriction sites and cloned into modified pMIG retroviral vectors, immediately downstream from a T7 bacteriophage promoter. Upstream from the cloning site, the pMIG retroviral vectors also having a coding sequence for T7 polymerase operably linked to an internal ribosomal entry site and GFP (green fluorescent protein).

The pooled population of the resulting vectors, each containing sense and antisense random 19-ers, is an siRNA expression library.

EXAMPLE 8

This method demonstrates a method of preparing a double stranded RNA library that exceeds the size limitations of siRNAs without inducing an antiviral response leading to cell death.

A human cDNAa library is prepared by standard methodology or is purchased from a reagents catalog. The cDNA library is digested into 100 to 1000 base pair fragments, using a restriction enzyme (e.g. Sau3A) [see Method 5, FIGS. 7A-7B]. The resulting fragments are cloned into plasmids having bi-directional transcription driven by flanking, oppositely-oriented T7 promoters, wherein the sense and antisense sequences of the cloned fragments are both transcribed (see, e.g., Examples 5, 6, and 7). The plasmids also have the E3L gene of vaccinia cloned in cis with the digested cDNA fragment.

The resulting population of plasmids, each containing a sense and antisense copy of a random 19-mer, is an siRNA library. Upon transfection into mammalian cells, the library will transcribe relatively long (between about 100 and about 1000 base pairs) double stranded RNA, which will form duplexes. However, the library also will express the E3L protein, which will inhibit the interferon-response to the long double stranded RNAs to prevent cell death. This will permit the endogenous DICER enzyme to process the long double stranded RNAs into 21 to 23 base pair siRNAs.

EXAMPLE 9

This example demonstrated the generation of a fluorescent-encoding retroviral recipient vectors that can be used to receive the siRNA-encoding sequences.

The vector pMIG (Perijs et al), a retroviral vector carrying an IRES and green fluorescent protein was digested with Hpa 1 and a ccd cloning cassette (Clontech, Inc) was inserted, generating pMigCCD. A U6 promoter fragment containing a hairpin siRNA stuffer between its BamH1 and HindIII sites was amplified from pSilencer 2.0 (Ambion, Inc) using primers 5'-CACCGAGGGAGAAGCATGAATTCC-3' (SEQ ID NO:14) (sense) and 5'-CGTTGTAAAACGACGGCCAG-3' (SEQ ID NO:15) (antisense). This PCR fragment was cloned into the shuttle vector pTopoEntr (Clontech) and recombined using the Clonase reaction with pMigCCD. This resulted in the insertion of a U6 promoter 5' of the IRES-GFP in pMig (plasmid pMigU6IG). The U6 promoter is oriented toward the IRES. This procedure also inserts a Not1 site 5' of the U6 promoter in the resulting plasmid. The plasmid pMigAdapterU6 contains a U6 promoter 3' of the IRES-GFP, oriented toward GFP (i.e. opposite that in pMIGU6IG). The pMig vector was digested with Sal1 and Cla and an adapter sequence comprised of the annealed oligonucleotides 5'TCGACGCGTGACTCGAGTCGGATCCGCGGCCGCAT3' (SEQ ID NO:16) and 5'GCGACTGAGCTCAGCCTAGGCGCCGGCGTAGC3' (SEQ ID NO:17) was inserted to insert unique sites Sal1-Mlu1-PshA1-Xho1-BamH1H-Not1-Cla1. A U6 promoter was PCR amplified from pSilencer 2.0 using 5'GAGAGCGGCCGCGTCCTTTCCACAAGATAT3' (SEQ ID NO:18) and 5'GCGCCATCGATAAGGTCGGGCAGGAAGAGGG3' (SEQ ID NO:19), digested with Not1 and Cla 1 and cloned into the Not1-Cla site to make pMigAdapterU6.

Another vector (retroviral) was made containing two U6 promoters in opposite orientation. This plasmid also expresses GFP. The plasmid pMigU6IG was digested with Sal and Cla and the U6 promoter derived by Sal1 plus Cla1 digestion of the pMigAdapter U6 was cloned into it, generating plasmid pMigU6IGU6. In another example, a retroviral plasmid expressing both red and green fluorescence and containing two U6 promoters was constructed by digesting pMigU6IGU6 with Bgl 2 and cloning in the gene for dsred2 flanked by BamH1 sites. The dsred2 insertion was derived by PCR amplification of the plasmid pdsred2N1 (Clonetech) with the primers 5'CACGGGATCCACCGGTCGCCACCATG3 (SEQ ID NO:20) and 5'CAGCGGATCCTACAGGAACAGGTGGTGGC3' (SEQ ID NO:21), and digestion of the resulting product with BamH1. The resulting plasmid is pdsredMigU6IGU6.

In another example, plasmids containing one U6 promoter and expressing only red fluorescence were constructed. One plasmid contained the U6 promoter oriented toward the desired gene by digesting pdsredMigU6IGU6 with Not1 and ligating it closed. In another example, a red fluorescent vector containing a U6 promoter oriented away from the desired gene was constructed by digesting pdsredMigU6IGU6 with both BamH1 and Cla1 and ligating it with an adapter generated by annealing the sequences 5'GATCCTTTTTAAGCTTGGAT3' (SEQ ID NO:22) and 5'CGATCCAAGCTTAAAAAG3' (SEQ ID NO:23) which inserts a poly-T polymerase III stop site followed by a HindIII site between the BamH1 and Cla1 sites, generating the plasmid pdsredMigU6BTHC.

EXAMPLE 10

This example demonstrates the generation of an siRNA library.

The vector pSilencer puro 3.1 (Ambion, Inc.), containing the H1 polymerase III promoter followed by BamH1 and HindIII was digested with restriction enzymes BamH1 and HindIII. An adapter consisting of annealed sense strand 5'GATCCTTTTTTATCGATAAACCTCGAGTA-3' (SEQ ID NO:24) and antisense strand 5'AGCTTACTCGAGGTTTATCGATAAAAAAG-3' (SEQ ID NO:25) was cloned into the digested vector. This inserts the following sites into the vector, beginning with the BamH1 site: BamH1/poly T stop site for polymerase III transcripts/Cla 1 site, Xho 1 site, HindIII site. The resulting plasmid (pSilpuroAdapter) was digested with Xho 1 and HindIII. A U6 promoter fragment bound by Xho 1 and HindIII was prepared using PCR amplification of the U6 promoter containing plasmid pSilencer 2.0 (Ambion, Inc) with primers 5'-GCGCCAAGCTTAAGGTCGGGCAGGAAGAGGG-3' (SEQ ID NO:26) (sense) and an antisense primer which contained an additional 27-bp of U6 promoter sequence, thought to enhance transcript stability: 5'-GGCCTCGAGCTGCCGAAGCGAGCACGGTGTTTCGTCCTTTCCACAAG-3' (SEQ ID NO:27). PCR product was digested with HindIII and Xho 1 restriction enzymes and cloned into pSilpuroAdapter such that the H1 and U6 promoters were in opposite orientations relative to each other.

To generate the siRNA library, the resulting plasmid, pSilpuroBCSU6-H1 was digested with BamH1 and Xho1 and random inserts engineered to contain Bgl 2 and Xho1 sites at their ends were digested and cloned into the plasmid. In one experiment, the random insert was generated by annealing the sequence 5' CTTGAGATCTCNNNNNNNNNNNNNNNNNNNNCTCGAGTGTACACATGGCGA-3' (SEQ ID NO:28) with the sequence 5'-TCGCCATGTGTACACTCGAG-3' (SEQ ID NO:29). These sequences were filled in using Klenow buffer, purified and digested with Bgl 2 and Xho 1 for cloning. In another experiment, the H1 promoter and adaptor cloning site from pSilpuroAdaptor or the H1-U6 cassette from pSilpuroBCSU6-H1 were amplified by PCR, cloned into pTopoEntr (Invitrogen) and then cloned using Clonase recombinase into the pLenti6/Block-it-DEST vector (Invitrogen) to facilitate cloning of random hairpins into a lentiviral vector.

Samples of the resulting libraries were isolated and the sequences of inserts determined. A small sample of clones within the library revealed that the inserts had distinct sequences. Examples of the sequences within this library are as follows:

| Sequence | ID |
|---|---|
| ATTTCTAAAGGCGTGTCCGA | (SEQ ID NO:30) |
| CCTCTTGGACTGATACAGCT | (SEQ ID NO:31) |
| GATGTTCGAGCCAGAGGTCT | (SEQ ID NO:32) |
| CCTCAGTGAGGCCAATTGAG | (SEQ ID NO:33) |
| GTTCTTGTCTTAAACGGAGG | (SEQ ID NO:34) |
| ATCCGCTTGTAATCTACAGG | (SEQ ID NO:35) |
| TCACTTTTATGGGGTCATTA | (SEQ ID NO:36) |
| CGGTTTGCAATTGCAAGCAT | (SEQ ID NO:37) |
| CTTTCGAGGCAGGGCTCTGA | (SEQ ID NO:38) |
| ACACCTCTGCTGATCAAATT | (SEQ ID NO:39) |
| TATGCGGCGTTCAGACCGCA | (SEQ ID NO:40) |
| ATCGCTGTGACTTCATGACA | (SEQ ID NO:41) |
| TAACAAATGCGCTACGTCCT | (SEQ ID NO:42) |
| ATCAGGCGGAGTATAGTTTC | (SEQ ID NO:43) |
| AGTACCTTTTGCGCCTCTCC | (SEQ ID NO:44) |

EXAMPLE 11

This example demonstrates that siRNAs with effective inhibition of gene expression can be generated using the recombinase approach described in Example 1. In this example, siRNA that inhibits estrogen receptor alpha (ERα) is used, but this is a proxy for random or semirandom sequences.

Two 21-bp sequences matching part of the estrogen receptor alpha were selected as templates for generation of siRNA by recombinase. These sequences were as follows:

```
AAGGCCTTCTTCAAGAGAAGT      (SEQ ID NO:45)

AAGATCACAGACACTTTGATC      (SEQ ID NO:46)
```

Using each 21-bp sequences as input, ds-RNA coding hairpins were generated. Hairpins were generated using the method shown in FIGS. 1A-1C. The sequences of the resulting hairpins were as follows:

```
AAGGCCTTCTTCAAGAGAAGT-GG  (siRNA #1)  (SEQ ID NO:47)
TAACC-ACTTCTCTTGAAGAAGGC
CTT

AAGATCACAGACACTTTGATC-GG  (siRNA #2)  (SEQ ID NO:48)
TAACC-GATCAAAGTGTCTGTGAT
CTT
```

These oligoDNAs having the sequences encoding the half-hairpins (SEQ ID Nos: 46 and 47) were cloned into expression plasmids. Plasmids termed "siR1" and "siR4" encoded the siRNA#1 sequence, plasmids termed "siR7" and "siR11" encoded the siRNA#2 sequence.

Figure 9:
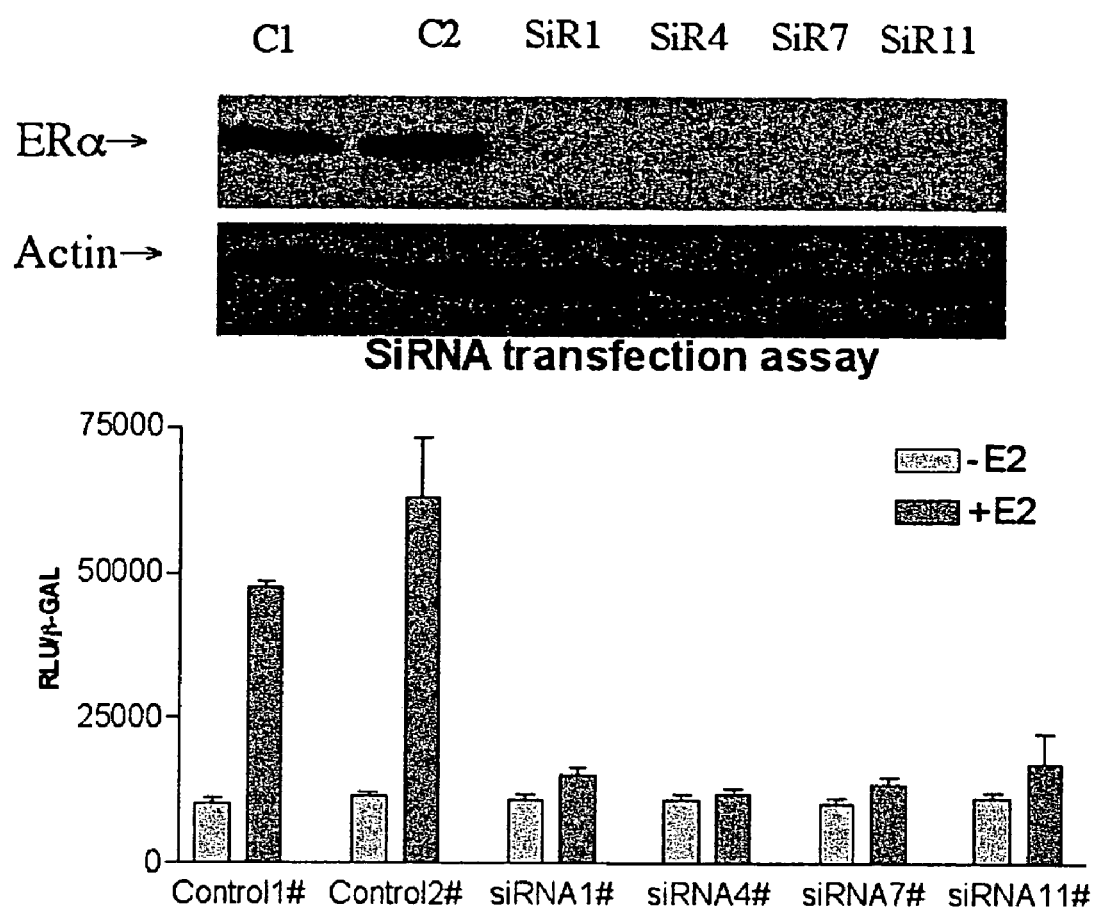
FIG. 9 presents the results of an experiment demonstrating the inhibition of estrogen receptor alpha using siRNA prepared in accordance with the inventive method.

To assay the effect of the siRNA#1 and siRNA#2 sequences on ERα expression, CV-1 cells were co-transfected with an ERα expression plasmid, a test siRNA-encoding plasmid (i.e., one of siR1, siR4, siR7, and siR11 or control plasmid C1 and C2), an ERE-tk-luciferase reporter plasmid, and a CMV-β-gal control plasmid. The next day, cells received either fresh medium or medium containing 100 nM 17-β-estradiol (E2). 24 h after treatment, the cells were harvested and assayed for (A) ERα and actin expression by Western blot or (B) luciferase and β-gal reporter gene activity. Transfection of siR1, siR4 (both with sequence siRNA #1, above), siR7 or siR11 (both with sequence siRNA #2 above), but not vector control (C1 and C2) resulted in a reduction in ERα protein expression and E2-induced ERα transcriptional activity. These results are depicted graphically in FIG. 9. The results demonstrate that both the siRNA#1 and siRNA#2 sequences are able to attenuate ERα expression and, therefore, that they are siRNA sequences.

While, as noted above, the ERα siRNAs are employed in this example as a proxy for random or semirandom sequences, the invention provides a nucleic acid molecule comprising or consisting essentially of at least 10 consecutive nucleic acids selected from the following: AAGGCCTTCT-TCAAGAGAAGT (SEQ ID NO:45), AAGATCACAGA-CACTTTGATC (SEQ ID NO:46), AAGGCCUUCUUCAA-GAGAAGU (SEQ ID NO:49) and AAGAUCACAGACACUUUGAUC (SEQ ID NO:50). In some embodiments, the inventive nucleic acid can comprise or consist essentially of at least about 15 consecutive nucleic acids from either of the two sequences. Desirably, the inventive nucleic acid is siRNA or shRNA and can attenuate the expression of ERα. However, the nucleic acid also can be DNA. For example, the nucleic acid can form a part of an expression cassette (typically comprising DNA) that can express the nucleic acid as RNA. An expression cassette includes a suitable promoter, the coding sequence, and a termination sequence. Such an expression cassette can be engineered into a suitable vector system (e.g., a plasmid or viral expression vector system) for introduction into cells to RNA within cells. It is within the ordinary skill in the art to construct plasmid and viral expression vectors.

The inventive nucleic acid can be used to attenuate the expression of ERα, and the invention provides a method for attenuating the expression of ERα using the inventive nucleic acid. In accordance with the inventive method, the inventive nucleic acid is introduced into a cell expressing ERα under conditions for the inventive nucleic acid to attenuate the expression of the ERα within the cell. The cell can be either in vivo or in vitro. Where the inventive nucleic acid is provided to the cell as RNA molecules (e.g., siRNA or shRNA), such are introduced into the cell using transduction methods known to those of skill in the art. Alternatively, the inventive nucleic acid molecule can be provided to the cell by transfecting, transuding, or infecting the cell with an expression vector containing an expression cassette encoding the nucleic acid as siRNA or shRNA. In such an embodiment, the RNA will be produced within the cell, where it can act as siRNA or shRNA to attenuate the expression of ERα.

All references, including publications, patent applications, and patents, cited herein are hereby incorporated by reference to the same extent as if each reference were individually and specifically indicated to be incorporated by reference and were set forth in its entirety herein. Also, reference herein to other publications is not an admission that such publications constitute prior art to this application.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context

What is claimed is:

1. A method for preparing a small interfering RNA (siRNA) library, the method comprising:

(1) generating a population of oligoDNAs, each of which comprises a random or semirandom sequence flanked by a 3' restriction site and a 5' restriction site, wherein the 3' restriction site is different than the 5' restriction site, (2) cloning the oligoDNAs into plasmids having two recombinase sites oriented toward each other so as to orient the random sequence flanked by the 3' restriction site and the 5' restriction site between the dual recombinase sites;

(3) replicating the plasmids within a population of host cells that produce the appropriate recombinase enzyme for the particular recombinase recognition sites present in the plasmids;

(4) exposing the plasmids to the recombinase enzyme within the host cells;

(5) isolating plasmid DNA from the population of host cells and digesting the isolated plasmids with a restriction enzyme specific for either the 3' restriction site or the 5' restriction site;

(6) autoligating fragments digested in step (5) which contain one or more dual cassettes wherein a dual cassette comprises inverted repeats of the oligoDNA, which encodes random or semirandom siRNA, wherein the autoligation (step (6)) results in the formation of a tandem inverted repeat of an oligoDNA wherein the repeat sequences are separated by a site for the restriction enzyme used in the digestion of step (5) and flanked by sites for the restriction enzyme used in the digestion of step (7), (7) digesting the autoligated fragments with one or more restriction enzymes specific for the restriction sites flanking the inverted repeats to release the dual cassettes as a population of dual cassettes, and cloning the population of dual cassettes into an RNA expression vector system, which includes an RNA expression vector having an RNA polymerase promoter and an RNA polymerase termination sequence, such that the dual cassettes are inserted between the RNA promoter and the termination sequence;

(8) pooling the vectors to form an siRNA-encoding library.

2. The method of claim 1, wherein the RNA polymerase promoter within the RNA expression vector is a T7 bacteriophage promoter and the RNA termination sequence is a terminator of T7 transcription.

3. The method of claim 1, wherein the RNA expression vector comprises opposing promoters.

4. The method of claim 1, wherein the dual cassettes are cloned into the RNA expression vectors as single inserts.

5. The method of claim 1, wherein the dual cassettes are cloned into the RNA expression vectors as oligomeric inserts comprising at least 2 of said dual cassettes.

6. The method of claim 1, wherein the population of dual cassettes encoding the random or semirandom siRNA is cloned into the RNA expression vectors in tandem with cassettes encoding siRNA comprising a predefined sequence.

7. The method of claim 2, wherein the RNA expression vector further contains an expression cassette encoding a fusion protein comprising the DNA-binding and transcriptional activation domains of the T7 bacteriophage RNA polymerase, a nuclear localization signal, and a portion of a wild-type or mutant steroid-hormone receptor containing a ligand-binding domain, conferring ligand-dependent activity of the T7 polymerase.

8. A library as prepared by the method of any of claims 1-7.

9. A method of generating DNA hairpins comprising (1) generating a population of oligoDNAs, each of which is flanked by a 3' restriction site and a 5' restriction site, wherein the 3' restriction site is different than the 5' restriction site, (2) cloning the oligoDNAs into plasmids having two recombinase sites oriented toward each other so as to orient the oligoDNAs flanked by the 3' restriction site and the 5' restriction site between the dual recombinase sites;

(3) replicating the plasmids within a population of host cells that produce the appropriate recombinase enzyme for the particular recombinase recognition sites present in the plasmids;

(4) exposing the plasmids to the recombinase enzyme within the host cells;

(5) isolating plasmid DNA from the population of host cells and digesting the isolated plasmids with a restriction enzyme specific for either the 3' restriction site or the 5' restriction site;

(6) autoligating fragments digested in step (5) which contain one or more dual cassettes wherein a dual cassette comprises inverted repeats of the oligoDNA, wherein the autoligation (step (6)) results in the formation of a tandem inverted repeat of an oligoDNA wherein the repeat sequences are separated by a site for the restriction enzyme used in the digestion of step (5).

10. The method of claim 9, wherein the recombinase is FLP or Cre.

11. The method of claim 9, wherein the population of oligoDNAs has a predesigned sequence and wherein the resulting hairpin is a specific siRNA-encoding hairpin.

12. The method of claim 9, wherein the sequences within the population of oligoDNAs are random or semirandom and wherein the resulting hairpins constitute a random or semirandom siRNA-encoding library.

* * * * *